(12) United States Patent
Hindsgaul et al.

(10) Patent No.: US 6,177,553 B1
(45) Date of Patent: *Jan. 23, 2001

(54) SOLID PHASE SYNTHESIS OF THIO-OLIGOSACCHARIDES

(75) Inventors: Ole Hindsgaul; Gerd Hummel, both of Edmonton (CA)

(73) Assignee: Synsorb Biotech, Inc., Calgary (CA)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/130,897

(22) Filed: Aug. 7, 1998

(51) Int. Cl.$^7$ .............................. C07H 5/10; C07H 3/06; C07H 3/04
(52) U.S. Cl. .................. 536/4.1; 536/18.5; 536/122; 536/123; 536/123.13; 536/124
(58) Field of Search .................................... 536/4.1, 18.5, 536/122, 123, 123.13, 124

(56) References Cited

U.S. PATENT DOCUMENTS

| | | | |
|---|---|---|---|
| 5,700,916 | * 12/1997 | Kahne et al. | 536/1.11 |
| 5,780,603 | * 7/1998 | Hindsgaul | 536/4.1 |
| 5,861,492 | * 1/1999 | Kahne | 536/4.1 |

FOREIGN PATENT DOCUMENTS

98/21222  5/1998  (WO).

OTHER PUBLICATIONS

Hindsgaul et al., "Synthesis and evaluation of thio–trisaccharides as acceptors for N–acetylglucosaminotransferase. V", Canadian J. Chem., vol. 75(6): 790–800, 1997.*

Hindsgaul et al., "Solid–phase synthesis of thio–oligosaccharides", Angew. Chem. Int. Ed., vol. 38(12): 1782–1784, 1999.*

Contour–Galcera et al., "Synthesis of sulfur–linked analogues of nigerose, laminarabinose, laminaratriose, gentiobiose, gentiotriose, and laminaran trisaccharide Y", Carbohydrate Research, vol. 281:99–118, 1996.*

Petrusova et al., "A nitro sugar derivative route to 2–thioepisophorose and 2–thiosophorose and their remarkable facile epimerization", Carbohydrate Research, vol. 283: 73–80, 1996.*

Gravert et al. "Organic synthesis on Soluble Polymer Supports: Liquid–Phase Methodologies", Chem. Rev., vol. 97: 489–509, 1997.*

Nicolaou et al., "Oligosaccharide Synthesis from Glycosyl Fluorides and Sulfides", Chapter 13 of Preparative Carbohydrate Chemistry (edited by Stephen Hanessian), publ. by Marcel Dekker, Inc., pp. 313–339, 1997.*

Rodebaugh et al., "Polymer–Supported Oligosaccharides via n–Pentenyl Glycosides: Methodology for a Carbohydrate Library", J. Org. Chem., vol. 62: 5660–5661, 1997.*

Seeberger et al., "Synthesis of Biologically Importatnt Oligosaccharides and Other Glycoconjugates by the Glycal Assembly Method", Aldrichimica Acta, vol. 30(3): 75–92, 1997.*

Rademann et al., "A New Method for the Solid Phase Synthesis of Oligosaccharides", Tetrahedron Letters, vol. 37(23): 3989–3990, 1996.*

Zhu et al., "A Two–Directional Approach for the Solid–Phase Synthesis of Trisaccharide Libraries", Angew. Chem. Int. Ed., vol. 37(13/14): 1898–1899, 1998.*

De Witt, Sheila Hobbs, "Combinatorial Libraries and High Throughput Synthesis", Chapter 8 of The Practice of Medicinal Chemistry (edited by Camille Wermuth), published by Academic Press, pp. 118–134, 1996.*

DeFaye, J., et al., "Thio–oligosaccharides: Their Synthesis and Reactions with Enzymes." *Studies in Natural Products Chemistry*. vol. 8, 1991, 315–357.

Frutchtel, J. S. et al. "Organic Chemistry on Solid Supports. "*Angew.Chem. Int. Ed. Eng.* 35, 1996, 17–42.

Hummel, G et al.,"Solid–Phase Synthesis of Thio–oligosacchrides." *Angew. Chem. Int. Ed.* 38:12, 1999, 1782:1784.

* cited by examiner

*Primary Examiner*—Howard C. Lee
(74) *Attorney, Agent, or Firm*—Burns, Doane, Swecker & Mathis, LLP

(57) ABSTRACT

Solid phase synthetic methods of forming sulfur-linked disaccharides and oligosaccharides are described, wherein a saccharide or oligosaccharide bearing a protected thiol-group at the anomeric carbon is immobilized onto a solid support at any position other than the anomeric carbon atom of the reducing sugar. The resultant immobilized thiol, or a derivative thereof, undergoes nuclcophilic saccharide addition to provide a di- or oligosaccharide.

12 Claims, 4 Drawing Sheets

R=CF$_3$,Ph,(p-Me)Ph,Imidazolyl

X=Cl,Br,I,SR$_2$

R=alkyl,aryl

SOLID PHASE SYNTHESIS OF THIO-OLIGOSACCHARIDES

BACKGROUND OF THE INVENTION

1. Field of the Invention

This invention is directed toward solid phase synthetic methods for forming sulfur-linked disaccharides and oligosaccharides. In these methods, a saccharide or oligosaccharide bearing a protected thiol-group is immobilized onto a solid support at any position other than the protected thiol group. The thiol protecting group is then removed and optionally converted to its thiolate salt. The resulting thiol/thiolate is allowed to undergo nucleophilic saccharide addition to provide for a solid phase bound di- or oligosaccharide.

In a preferred embodiment, the nucleophilic saccharide addition reaction involves a saccharide or oligosaccharide group which has been activated at the desired point of linkage by introduction of a leaving group which is displaced by the thiol/thiolate to form a sulfide linkage.

In another preferred embodiment, the protected thiol group on the saccharide or oligosaccharide is located at the anomeric carbon atom of the reducing saccharide group.

References

The following publications, patents and patent applications are cited in this application as superscript numbers:

1 Hindsgaul, 1-*Thiogalactose Derivatives,* International Patent Application Publication No. WO 98/21221, published 22 May 1998.
2 Witczak, et al., *Thiosugars II,* Carbohydrate Research, 301:167–175 (1997).
3 L. X. Wand, N. Sakari and H. Kuzuhara, J. Chem. Soc. Perkin Trans., 1:1677–1682 (1990).
4 L. A. Reed and L. Goodman, *Carbohydr. Res.,* 94: 91–99 (1981).
5 S. Mehta, J. S. Andrews, B. D. Jonston and B. M. Pinto, *J. Am. Chem. Soc.,* 116: 1569–1570 (1994).
6 Hindsgaul, *Combinatorial Synthesis of Carbokydrate Libraries,* International Patent Application Publication No. WO 98/22487 published May 28, 1998.
7 F. Shafizadeh, R. H. Fumeaux and T. T. Stevenson, *Carbohydrate Res.,* 71 (1979) 169–191.
8 M. G. Essig, *Carbohydr. Res.,* 156 (1986) 225–231.
9 T. W. Greene and G. M. Wuts, *Protecting Groups in Organic Synthesis,* Second Edition, Wiley, N.Y., 1991.
10 Gallop, et al., U.S. Pat. No. 5,525,734, for "*Methods for Synthesizing Diverse Collections of Pyrrolidone Compounds*", issued Jun. 11, 1996

2. State of the Art

Thiosugars, or 1-thioglycosides, have heretofore been disclosed for a variety of uses. For example, Hindsgaul[1,6] discloses that certain thiogalactose derivatives are useful in blocking the binding of toxins, such as heat-labile enterotoxin or cholera toxin, to their receptors either in vivo or in vitro. Similarly, Witczak, et al.[2,7] have disclosed thiosugars (both α and β linked thiodisaccharides) as being useful as probes in enzyme-inhibition studies and as components of sugar antibiotics.

The synthesis of compounds having such thio linkages is generally more difficult than the corresponding ether linkages. For example, the sulfur atom in thiol groups is less electronegative than the oxygen atom in alcohols, and therefore has a lower affinity for protons. For this reason, the thiol group is typically deprotonated to the corresponding thiolate group (e.g., —S$^-$) prior to alkylation.

In any event, solution phase synthesis of thio linked disaccharides has been achieved by several methods, such as $S_N2$-type reactions between thiolate anions and glycosyl halides[3], displacement of a leaving group by a 1-thioglycopyranose[4], and condensation of benzylated 1,6-anhydro-glucopyranose with a protected 4-thioglucopyranoside.[5] These conventional methods are generally multi-step methods producing a variable yield of the desired product. Other methods of producing thiodisaccharides by Michael addition of sugar thiols to levoglucosenone are also known.[7,8]

However, the above conventional means of forming thio di- or oligosaccharides require the formation of the thio di- or oligosaccharide in solution. This presents the difficulty of removing undesired side products and excess reagents without affecting the desired end product or reducing yield during purification.

A solid phase reaction for formation of a thio-linked saccharide compound would be particularly desirable because it would allow facile purification of the ultimate product, as well as of any intermediates produced during synthesis, without reducing overall yield. However, there apparently has been no reported methods for forming thio di- or oligosaccharides on a solid support.

SUMMARY OF THE INVENTION

This invention is directed to the unexpected and novel discovery that heretofore known solution phase nucleophilic displacement reactions to form disaccharides can also be performed with saccharide or oligosaccharide bound to a solid support. Synthesis of di- and oligosaccharides on solid supports provides particular advantages in conformational control of the reaction, enhanced purity of the resulting products and improved overall yields.

Accordingly, in one of its method aspects, this invention is directed to a method for forming a sulfur-linked di- or oligosaccharide on a solid support which method comprises:

i) immobilizing a first saccharide or oligosaccharide on a solid support wherein the first saccharide or oligosaccharide comprises a protected thiol group of the formula —SR at the anomeric carbon of the reducing saccharide unit wherein R is a thiol group protecting agent;

ii) deprotecting the thiol group and optionally converting the deprotected thiol group to the corresponding thiolate;

iii) optionally adding a metal complexing agent; and iv) contacting the immobilized saccharide or oligosaccharide group formed in ii) or iii) above with a second saccharide or oligosaccharide comprising a nucleophilic displaceable group under conditions wherein the thiol or thiolate group displaces said nucleophilic displaceable group thereby forming a sulfide linkage between the first and second saccharides/oligosaccharides.

In one preferred embodiment, the saccharide or oligosaccharide immobilized on the solid support is an unprotected saccharide or oligosaccharide group although hydroxyl/amino protected saccharides or oligosaccharides can be used provided there is at one functional group available for coupling to the solid support. In a particularly preferred embodiment, the point of immobilization or attachment of the saccharide or oligosaccharide onto the solid support is directed by the use of solid supports comprising functional groups which preferentially react with primary alcohols.

In another preferred embodiment, the thiol blocking group, R, is selected from the group consisting of acyl, alkyl, substituted alkyl, aryl, heteroaryl groups, thioalkyl, thiosubstituted alkyl, thiocycloalkyl, thioaryl and thioheteroaryl and the like.

In still another preferred embodiment, the oligosaccharide attached to the solid support is attached via a cleavable linking arm. In a preferred aspect of this embodiment, the process described above further comprises immobilizing the saccharide or oligosaccharide described in i) above to the solid support via a cleavable linker and, subsequent to iv) above, removing the product formed in iv) from the solid support.

In another preferred embodiment, the second saccharide or oligosaccharide employed in iv) above comprises a protected thiol group of the formula -SR at the anomeric carbon of the reducing saccharide unit wherein R is a thiol group protecting agent and steps ii), iii) and iv) are repeated as often as desired.

Preferred saccharides for use in the methods of this invention include, by way of example, D-galactose, D-glucose, D-mannose, D-xylose, D-gluconic acid (e.g., D-glucoronic acid), N-acetyl-D-glucosamine, N-acetyl-D-galactosamine, sialyic acid, L-fucose, keto-deoxyoctulolsonic acid (KDO), and the like. Included within the definition of this term are deoxy, deoxyhalo, deoxyamino, acylated, phosphorylated and sulfated derivatives of such saccharides. Also included within this definition are cyclitols such as inositols.

As used herein, sugars (saccharides) are sometimes referenced using conventional three letter nomenclature. All sugars are assumed to be in the D-form unless otherwise noted, except for fucose, which is in the L-form. Further, all sugars are in the pyranose form.

Preferred oligosaccharides for use in or made by the methods described herein include those having two or more, and preferably 2–10, of the saccharide units recited above wherein each saccharide unit is independently selected relative to the other saccharide units in the oligosaccharide.

Preferred solid supports for use herein are selected from the group consisting of silica, synthetic silicates, biogenic silicates, porous glass, hydrogels, silicate-containing minerals, synthetic polymers, polystyrene, polypropylene, polyacrylamide, polyethylene glycol, polyacrylamide and copolymers thereof including copolymers of polystyrene/polyethylene glycol and polyacrylamide/polyethylene glycol.

DETAILED DESCRIPTION OF THE INVENTION

Figure 1:
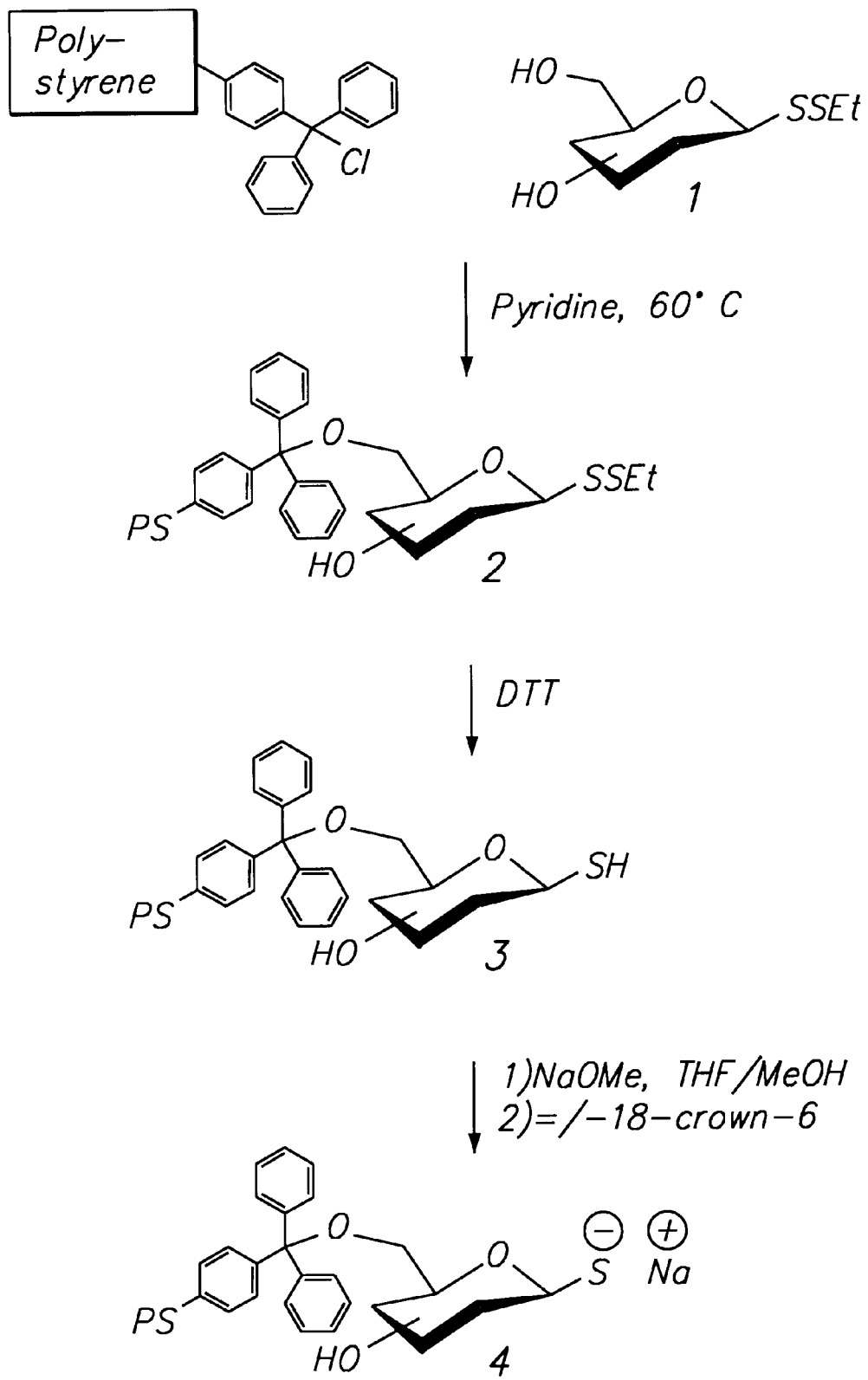
FIG. 1 illustrates a reaction scheme for the formation of an immobilized saccharide group having a protected thiol group at the anomeric carbon atom. In the saccharide group depicted in this figure, the hydroxyl groups are unprotected (PS in this figure refers to polystyrene).

As described above, this invention relates to a method of forming sulfur-linked oligosaccharides on a solid support. However, prior to describing this invention in further detail, the following terms will first be defined.

Definitions

The term "thiol protecting group" refers to well known functional groups which, when bound to the thiol sulfur, render the resulting protected thiol group (—SR) inert to the reaction conditions to be conducted on other portions of the compound and which, at the appropriate time, can be reacted to regenerate the thiol group. The identity of the R thiol protecting group is not critical and is selected to be compatible with the thiol saccharide or oligosaccharide and the chemistry to be conducted thereon as well as the relative ease of synthesis of compounds of forming this protecting group on the thiol and the relative ease of subsequent removal of this protecting group. Preferably, R is selected from the group consisting of acyl, alkyl, substituted alkyl, aryl, heteroaryl groups, thioalkyl, thiosubstituted alkyl, thiocycloalkyl, thioaryl and thioheteroaryl and the like.

The term "metal complexing agent" refers to well known complexing agents which complex with cations forming the counter ion for the thiolate anion. Preferably, the cations are alkali ions such as lithium, sodium and potassium ions or ammonium ions including tetraalkylammonium ions. Complexation of the cation enhances the nucleophilicity of the thiolate anion. Examples of suitable metal complexing agents include 18-crown-6, 15-crown-5, cryptofix and the like. The selection of the specific metal complexing agent is conducted relative to the cation to be complexed and such selection is well within the skill of the art.

The term "nucleophilic displaceable group" refers to conventional leaving groups which will be displaced by a nucleophile thereby forming a covalent bond therebetween with elimination of the leaving group. For example, when the nucleophile is a thiolate group (—S⁻) and the leaving group is a bromo group attached to a carbon atom (—Br—C<), displacement of the bromo leaving group by the thiolate group results in the formation of a sulfur—carbon covalent bond. The selection of the appropriate leaving group is not critical and any of a variety of well known leaving groups can be known. Examples of such leaving groups include various sulfonic ester groups, such as tosylate, mesylate, brosylate, nosylate groups, and fluorinated sulfonic ester groups, such as triflate, nonaflate and tresylate groups and the like.

"Alkyl" refers to monovalent alkyl groups preferably having from 1 to 10 carbon atoms and more preferably 1 to 6 carbon atoms. This term is exemplified by groups such as methyl, ethyl, n-propyl, iso-propyl, n-butyl, iso-butyl, n-hexyl, and the like.

"Substituted alkyl" refers to a branched or straight chain alkyl group of from 1 to 8 carbon atoms having from 1 to 3 substituents selected from the group consisting of hydroxy, acyl, acylamino, acyloxy, alkoxy, substituted alkoxy, alkenyl, alkynyl, amino, substituted amino, aminoacyl, aryl, aryloxy, carboxy, carboxyalkyl, cyano, cycloalkyl, guanidino, halo, heteroaryl, heterocyclic, nitro, thiol, thioalkyl, thio(substituted alkyl), thioaryl, thioheteroaryl, and the like. Preferred substituents include hydroxy and amino.

"Acyl" refers to the groups alkaryl-C(O)—, alkyl-C(O)—, aryl-C(O)—, and heteroaryl-C(O)— where alkaryl, alkyl, aryl and heteroaryl are as defined herein.

"Acylamino" refers to the group —C(O)NRR where each R is independently hydrogen or alkyl.

"Acyloxy" refers to the groups alkyl-C(O)O—, aryl-C(O)O—, heteroaryl-C(O)O—, and heterocyclic-C(O)O—, where alkyl, aryl, heteroaryl and heterocyclic are as defined herein.

"Alkaryl" refers to -alkylene-aryl groups wherein alkylene and aryl are defined herein. Such alkaryl groups are exemplified by benzyl, phonethyl and the like.

"Alkoxy" refers to the group alkyl-O—. Such alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group (substituted alkyl)-O— where substituted alkyl is defined herein.

"Alkenyl" refers to alkenyl groups preferably having from 2 to 8 carbon atoms and more preferably 2 to 6 carbon atoms and having at least 1 and preferably from 1–2 sites of alkenyl unsaturation which groups are optionally substituted with from 1 to 3 substituents selected from the group consisting of hydroxy, acyl, acylamino, acyloxy, alkoxy, substituted alkoxy, alkynyl, amino, substituted amino, aminoacyl, aryl, aryloxy, carboxy, carboxyalkyl, cyano, cycloalkyl, guanidino, halo, heteroaryl, heterocyclic, nitro, thiol, thioalkyl, thio(substituted alkyl), thioaryl, thioheteroaryl, and the like. Such alkenyl groups include ethenyl (—CH═CH$_2$), n-propenyl (i.e., allyl) (—CH$_2$CH═CH$_2$), iso-propenyl (—C(CH$_3$)═CH$_2$), and the like.

"Alkylene" or "alkyldiyl" refers to divalent alkylene groups preferably having from 1 to 8 carbon atoms and more preferably 1 to 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkynyl" refers to alkynyl groups preferably having from 2 to 8 carbon atoms and more preferably 2 to 6 carbon atoms and having at least 1 and preferably from 1–2 sites of alkynyl unsaturation which groups are optionally substituted with from 1 to 3 substituents selected from the group consisting of hydroxy, acyl, acylamino, acyloxy, alkoxy, substituted alkoxy, alkenyl, amino, substituted amino, aminoacyl, aryl, aryloxy, carboxy, carboxyalkyl, cyano, cycloalkyl, guanidino, halo, heteroaryl, heterocyclic, nitro, thiol, thioalkyl, thio(substituted alkyl), thioaryl, thioheteroaryl, and the like. Such alkynyl groups include ethynyl (—C≡CH), propargyl (—CH$_2$C≡CH) and the like.

"Amino" refers to the group —NH$_2$.

"Substituted amino" refers to the group -N(R)$_2$ where each R is independently selected from the group consisting of hydrogen, alkyl, substituted alkyl, alkenyl, aryl, cycloalkyl, heteroaryl, heterocyclic and where both R groups, together with the nitrogen to which they are bond, are joined to form a heterocyclic group. When both R groups are hydrogen, —N(R)$_2$ is an amino group as defined above. Examples of substituted amino groups include, by way of illustration, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic, and the like.

"Aminoacyl" refers to the group —NRC(O)R where each R is independently hydrogen or alkyl.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

Unless otherwise constrained by the definition for the aryl substituent, such aryl groups can optionally be substituted with from 1 to 3 substituents selected from the group consisting of hydroxy, acyl, acyloxy, alkyl, substituted alkyl, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy.

"Aryloxy" refers to the group aryl-O— where the aryl group is as defined herein including optionally substituted aryl groups as also defined herein.

"Carboxy" refers to the group —COOH.

"Carboxyalkyl" refers to the group —C(O)O-alkyl where alkyl is as defined herein.

"Cycloalkyl" refers to cyclic alkyl groups or cyclic alkyl rings of from 3 to 8 carbon atoms having a single cyclic ring or multiple condensed rings which can be optionally substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl and the like, and spiro compounds. Examples of suitable cycloalkyl rings include single ring structures such as cyclopentine, cyclohexane, cycloheptane, cyclooctane, and the like, or multiple ring structures such as bicyclo[2.2.1]heptane, bicyclo[3.2.1]octane, and the like. Preferred cycloalkyl rings include cyclopentane, cyclohexane, cycloheptane and bicyclo[3.2.1]octane.

"Cycloalkenyl" refers to cyclic alkenyl groups or cyclic alkenyl rings of from 4 to 8 carbon atoms having a single cyclic ring and at least one point of internal unsaturation which can be optionally substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy. Examples of suitable cycloalkenyl groups include, for instance, cyclobut-2-enyl, cyclopent-3-enyl, cyclooct-3-enyl and the like. Such cycloalkenyl rings include, by way of example, cyclopentene, cyclohexene, and the like.

"Halo" or "halogen" refers to fluoro, chloro, bromo and iodo, and preferably is either chloro or bromo.

"Heteroaryl" refers to a monovalent aromatic carbocyclic group of from 2 to 8 carbon atoms and 1 to 4 heteroatoms selected from oxygen, nitrogen and sulfur within the ring.

Unless otherwise constrained by the definition for the heteroaryl substituent, such heteroaryl groups can be optionally substituted with 1 to 3 substituents selected from the group consisting of alkyl, substituted alkyl, alkoxy, aryl, aryloxy, halo, nitro, heteroaryl, thioalkoxy, thioaryloxy and the like. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heterocycle" or "heterocyclic" refers to a monovalent saturated or unsaturated group having a single ring or multiple condensed rings, from 1 to 8 carbon atoms and from 1 to 4 hetero atoms selected from nitrogen, sulfur or oxygen within the ring. For the purposes of this application, the term "heterocycle" or "heterocyclic" does not include carbohydrate rings (i.e. mono- or oligosaccharides).

Unless otherwise constrained by the definition for the heterocyclic substituent, such heterocyclic groups can be optionally substituted, with 1 to 3 substituents selected from the group consisting of alkyl, substituted alkyl, alkylene, alkoxy, aryl, aryloxy, halo, nitro, heteroaryl, thioalkoxy, thioaryloxy and the like. Such heteroaryl groups can have a single ring (e.g., pyrrolidinyl, piperidinyl, morpholinyl or tetrahydrofuranyl) or multiple condensed rings (e.g., indolinyl).

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline and the like.

"Thiol" refers to the group —SH.

"Thioalkyl" refers to the group —S-alkyl wherein the alkyl group is as defined herein.

"Thio(substituted alkyl)" refers to the group —S-(substituted alkyl) wherein substituted alkyl is defined herein.

"Thiocycloalkyl" refers to the group —S-cycloalkyl wherein the cycloalkyl group is as defined herein.

"Thioaryl" refers to the group aryl-S— wherein the aryl group is as defined herein, including optionally substituted aryl groups as also defined herein.

"Thioheteroaryl" refers to the group heteroaryl-S— wherein the heteroaryl group is as defined herein, including optionally substituted heteroaryl groups as also defined herein.

"Thiosugar" refers to any known sugar, particlar 5–6 membered rings, such as mammalian sugars (glucose, fructose, sucrose and mannose, for example) and their derivatives, bacterial sugars such as KDO and dideoxy sugars, for example, and derivatives thereof, and cyclitols, such as inositols and alditols such as sorbitol, mannitol, glucitol, and the like, and derivatives thereof, wherein the sugar as defined herein has a substituent sulfur group at the anomeric carbon except for cyclitols wherein any hydroxyl substituent can be convert to a thiol substituent.

"Thiosaccharide" refers to a thiosugar as described herein, wherein the thiosugar may contain more than one unit of sugar linked by sulfur linkages. The multiple sugar units may be the same or different.

In this invention, the thiosaccharide derivatives are covalently attached to a solid support. Solid supports containing such thiosaccharide derivatives preferably comprise a linking arm which links the solid support to the thiosaccharide derivative. The linking arm is desirably cleavable.

"Oligosaccharide" refers to compounds comprising 2–10 saccharide units wherein each saccharide is independently selected relative to the other saccharides in the oligosaccharide.

The term "solid support" refers to a material having a rigid or semi-rigid surface which contain or can be derivatized to contain reactive functionality which covalently links the first saccharide or oligosaccharide to the surface thereof. Such materials are well known in the art and include, by way of example, silica, synthetic silicates, biogenic silicates, porous glass, hydrogels, silicate-containing minerals, synthetic polymers, polystyrene, polypropylene, polyacrylamide, polyethylene glycol, polyacrylamide and copolymers thereof including copolymers of polystyrene/polyethylene glycol and polyacrylamide/polyethylene glycol, and the like.

"Cleavable linking arms" refer to linking arms, which are a chemical group or a covalent bond which optionally covalently attaches the thiosugar or its derivative to a support. At least one of the covalent bonds of the linking arm which attaches the compound to the solid support can be readily broken by specific chemical reactions, thereby providing for di- and oligosaccharides free of the solid support. The chemical reactions employed to break the covalent bond of the linking arm are selected so as to be specific for bond breakage thereby preventing unintended reactions occurring elsewhere on the compound. The cleavable linking group is selected relative to the synthesis of the oligosaccharides to be formed on the solid support so as to prevent premature cleavage of the oligosaccharide from the solid support as well as not to interfere with any of the procedures employed during synthesis on the support. Suitable cleavable linking arms are well known in the art, and may include such groups as tritylchlorides, Ellman's tetrahydropyranyl linker, silicon linkers and the like. Examples of cleavable linking arms are also described by Gallop, et al.[10]

Methodology

The methods of this invention will now be described in detail with reference to the above definitions and accompanying FIGS. 1–4.

The reversibly protected hydroxyl/thiol compounds of this invention can be prepared from starting materials which are either readily available in the art or are described herein using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, in addition to the protecting groups described herein, conventional protecting groups may also be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis,* Second Edition, Wiley, N.Y., 1991, and references cited therein.[9]

As noted above, this invention comprises a method for forming a sulfur-linked di- or oligosaccharide comprising tethering a first saccharide or oligosaccharide to a solid support wherein this saccharide or oligosaccharide comprises a protected thiol group at the anomeric carbon atom of the reducing saccharide unit, linking a second saccharide or oligosaccharide to the first saccharide or oligosaccharide, via a sulfur linkage, and optionally releasing the thiodisaccharide from the support.

The saccharide or oligosaccharide immobilized on the solid support has a thiol substituent on the anomeric carbon of the reducing sugar un it. Preferably, the saccharide or oligosaccharide to be linked or tethered to the solid support is unprotected at the hydroxyl groups thereof. Linkage can occur between any substituent on the saccharide or oligosaccharide other than the thiol group at the anomeric carbon of the reducing sugar. Preferably, the site of linkage on the saccharide is directed by use of a coupling functionality on the solid support which preferentially reacts with the primary OH group of the saccharide (e.g., the 6-hydroxyl group). Suitable functionality includes trityl chloride groups such as illustrated in FIG. 1.

In any event, other cleavable linkers or, in fact, non-cleavable linkers, may be used to immobilize the first saccharide or oligosaccharide unit to the solid support. Cleavable linkers are known in the art, such as Ellmans's tetrahydropyranyl linker, silicon linkers, and the like as well as are non-cleavable linkers. Other cleavable linking groups include, by way of example, those illustrated in Gallop, et al., U.S. Pat. No. 5,525,734, which also describes methods for tethering a compound to a solid support through such cleavable linking arms.

The solid support may be a classical polystyrene resin, a derivatized silicate or glass, PEG resin, polyacrylamide resin, hybrid resin or the like. Preferably, the solid support is a tritylchloride derivatized solid support which results in immobilization mainly through the primary OH group of the saccharide, as seen in FIG. 1.

The first saccharide or oligosaccharide group comprises any of a variety of saccharide or oligosaccharide groups having a thiol group at the anomeric carbon atom of the reducing saccharide unit. Examples for preparing such saccharides or oligosaccharides are well known in the art and are described, for example, by Ippolito, et al., International Patent Application Publication No. WO 93/24506; and Ippolito, et al., U.S. Pat. No. 5,580,858, issued Dec. 3, 1996 both of which are incorporated herein by reference in their entirety.

Preferably, the anomeric thiol substituent of the first saccharide or oligosaccharide is protected during linkage of the sugar to the solid support. The preferred protecting group for the anomeric thiol is an unsymmetrical disulfide, e.g., R is thiomethyl, thioethyl and the like.

The linkage of the first saccharide or oligosaccharide to the solid support is accomplished by any of a large number of known coupling techniques. In some cases, linkage of the first saccharide or oligosaccharide to the solid support is facilitated by use of suitable leaving groups on the saccharide or oligosaccharide. Examples of such leaving groups include, by way of illustration, various sulfonic ester groups, such as tosylate, mesylate, brosylate, nosylate groups, and fluorinated sulfonic ester groups, such as triflate, nonaflate and tresylate groups and the like.

A complementary reactive functionality is present on the solid support or is introduced thereon which reactive functionality reacts with the leaving group to form a covalent linkage between the saccharide and the solid support. As noted above, this linkage can be either a cleavable or non-cleavable linkage.

When a leaving group is employed on the first saccharide or oligosaccharide, these leaving groups are preferably introduced by differentially protecting the several hydroxyl groups of the saccharide or oligosaccharide so as to selectively expose a single hydroxyl group and then converting this hydroxyl group into a leaving group by chemistry well known in the art.

A significant problem associated with the selection of a suitable hydroxyl or thiol protecting group is that the reaction conditions necessary to effect removal of these protecting groups must be compatible with solid phase chemistry and the remainder of the molecule.

For example, benzyl groups, well known as hydroxyl protecting groups, are incompatible for use with sulfide containing compounds and/or unsaturated compounds if removal is to be effected, as is common practice, by hydrogenation in the presence of, e.g., palladium on carbon. Such incompatibility arises from the well established fact that such sulfur groups will poison these catalysts and will reduce the sulfide group to a thiol group and any unsaturation in the compound will also be reduced by these removal conditions regardless of whether this reduction is desired or not. This incompability dictates against the use of such protecting groups for compounds comprising thiol functionality and/or unsaturation. Moreover, the presence of the benzyl group on a solid support requires an inefficient solid phase to solid phase deprotection procedure when using a solid phase catalyst such as palladium on carbon.

Figure 2:
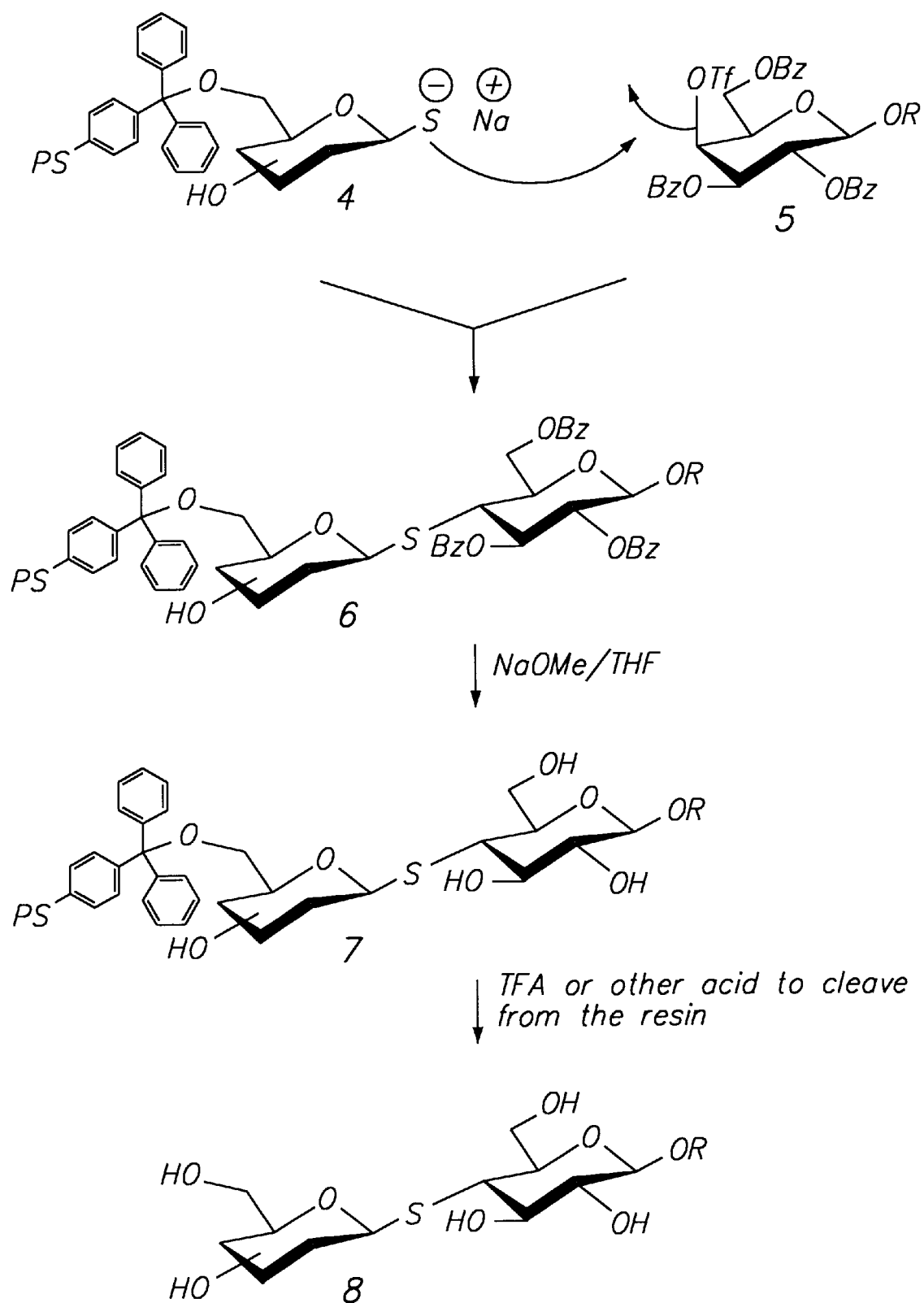
FIG. 2 illustrates a nucleophilic saccharide addition reaction to provide for a solid phase bound disaccharide wherein the saccharide units are linked together by a sulfide linkage (PS in this figure refers to polystyrene).

Accordingly, in the methods described herein, the blocking groups employed on the hydroxyl, amino and thiol functionalities are preferably removable via solution phase reagents. One class of such blocking groups are ortho and/or para substituted benzyl groups described in U.S. patent application Ser. No. 60/095,806 filed concurrently herewith as Attorney Docket No. 026579-212 and entitled "Compounds Comprising an Ortho or Para-Substituted Benzyl Protecting Group For at Least One Hydroxyl and/or Thiol Group" the text of which is hereby incorporated by reference in its entirety. Protecting groups described in that application include, for example, p-acetoxybenzyl, p-methoxybenzyl, and the like. Other suitable protecting groups removable under solid phase conditions include, for example, acetates, chloroacetates, benzoates or other esters, urethanes or carbonates; silyl groups including trimethylsilyl, t-butyldimethyl silyl, etc., O-allyl, benzylidene, acetonides, other acetals and ketals, etc. Photochemically removable nitrobenzyl groups can also be used. Alternatively, but less preferable, the first saccharide or oligosaccharide thiol and the second saccharide or oligosaccharide can also contain amino groups that may be protected by conventional methods. For example, removal of these protecting groups on the solid phase gives rise to compound 7 (FIG. 2).

The sugars employed in this invention are any thiol containing saccharides or oligosaccharides wherein the thiol substitution is preferably at the anomeric carbon. Methods for chemically modifying saccharides to introduce suitable substitution are well known in the art. See, for example, Ratcliffe, et al., U.S. Pat. No. 5,079,353, and J. Defaye, et al., "Thiooligosaccharides: Their Synthesis and Reactions with Enzymes" in *Studies in Natural Products Chemistry*, Vol. 8, pp. 315–357, Elsevier Sciences Publishers (1991). For example, 1-thiosaccharides can be prepared by reacting the saccharide with an acylating agent to convert all of the hydroxyl groups to acyl groups. The 1-acyl group is then selectively converted to the 1-thioacetyl group by reaction with an excess of thiolacetic acid. Hydrolysis then provides for the 1-thiosaccharide.

Alternatively, selective protection of the hydroxyl groups of the saccharide provides for one or more free hydroxyl groups which can be converted into appropriate leaving groups, such as mesyl or halo groups, by conventional chemistry well known in the art. Such leaving groups can then be displaced to afford the corresponding thiol group. See, for example, International Patent Application Serial No. PCT/CA92/00242. Specifically, a mesyl group is selectively introduced at one of the hydroxyl groups and then reacted with a thioacetyl group (for example potassium thioacetate) to provide for the corresponding thioacetate derivative. Treatment of this compound with a mild base provides for the corresponding thiol group.

After linking to the solid support, the free thiol on the thiosaccharide can be generated by reaction of the immobilized thiosaccharide (compound 2, FIG. 1) with a reducing agent like DTT (dithiothreitol), though many other reducing agents known in the art can be used. The free thiol (compound 3, FIG. 1) can then be deprotonated by any appropriate base as known to one of ordinary skill in the art to increase its nucleophilicity. The preferred base is sodium methoxide, which generates the sodium thiolate of the sugar, though any suitable base may be used. The nucleophilicity of the thiol can be further boosted by addition of a metal complexing agent such as 18-crown-6, 15-crown-5 or any other metal complexing species as known in the art, such as cryptofix. Other counterions such as Li, K (with or without co-ordinating species) and ammonium or alkylammonium ions may also be used. The resultant immobilized species (compound 4, FIG. 1) is very reactive.

Figure 3:
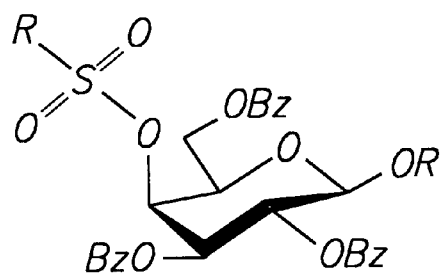
FIG. 3 illustrates various saccharides useful in the nucleophilic saccharide addition reaction depicted in FIG. 2. Each of the saccharides of FIG. 3 contain a nucleophilic displaceable group which is displaced under suitable reaction conditions by the thiol/thiolate of a solid phase bound saccharide or oligosaccharide.
Figure 3:
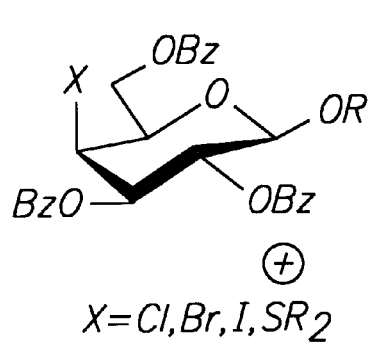
Figure 3:
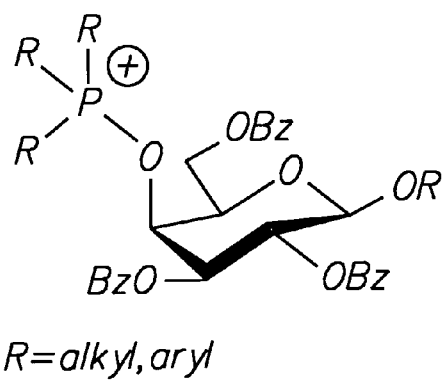
Figure 3:
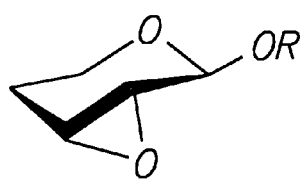
Figure 3:
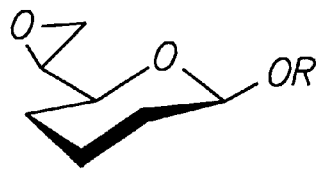
Figure 3:
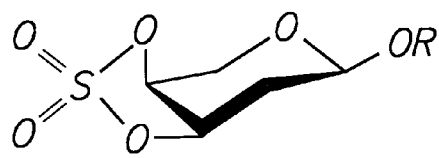
Figure 3:
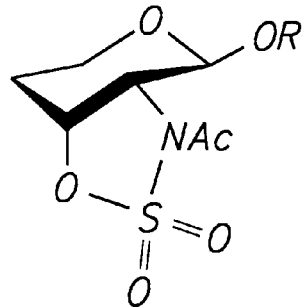

The immobilized sodium thiolate (compound 4, FIGS. 1 and 2) is reacted with a saccharide (e.g., compound 5, FIG. 2) or oligosaccharide derivative having a leaving group that is active in $S_N2$ reactions. The net result is alklylation (saccharide addition) of the thiolate to provide a di- or oligosaccharide such as compound 6 (FIG. 2). A preferred leaving group on the saccharide or oligosaccharide (e.g., compound 5) is a trifluoromethylsulfonate (triflate, Tf) group. Other leaving groups which may be used include, but are not limited to, methanesulfonate, p-toluenesulfonate, imidazolylsulfonate and other sulfonate derivatives known in the art, as well as halo groups such as iodo, bromo and chloro groups. Leaving groups may also be generated on the added sugar in situ, such as by the Mitsonobu reaction or $PPh_3/CCl_4$ leading to phosphoniumn leaving groups. Still other derivatives of the sugar capable of alkylating the immobilized sugar thiolate include sugar epoxides where the epoxide is present on the sugar ring or on an acylclic side chain. Cyclic sulfodiesters or sulfo ester amides can also be used. A compilation of some useful leaving groups for saccharides or oligosaccharides are shown in FIG. 3.

In the preferred embodiment, the immobilized sugar thiol has no hydroxyl protecting groups and the sugar bearing a leaving group is protected with groups that are removable once the sugar is bound to the immobilized sugar on the solid support. The protecting groups include those which can be removed via solution phase reagents such as those recited above. Alternatively, but less preferred, the immobilized sugar can have these same protecting groups. Both the immobilized thiosugar and added sugar can also contain amino groups that may be either protected by standard protecting groups or unprotected. Removal of these protecting groups on the solid support gives rise to compound 7 of FIG. 2.

The protecting groups need not be removed while the sulfur-linked sugar is bound to the solid support. However, removal of the protecting groups at this stage enables achievement of a high degree of purity with little or no loss in yield of the final product.

The final sulfur-linked di- and oligosaccharides (e.g., compound 8) are obtained on cleavage from the solid support when a cleavable linker is employed. The cleavage conditions are selected relative to the cleavable linker and such conditions are well known in the art. For example, cleavage of a trityl bound disaccharide is accomplished under standard acidic conditions (e.g., TFA, FIG. 2). The cleaved di- or oligosaccharide can be used directly for biological studies without purification or after simple purification by chromatography, passage through C-18 silica or ion exchange and the like.

Figure 4:
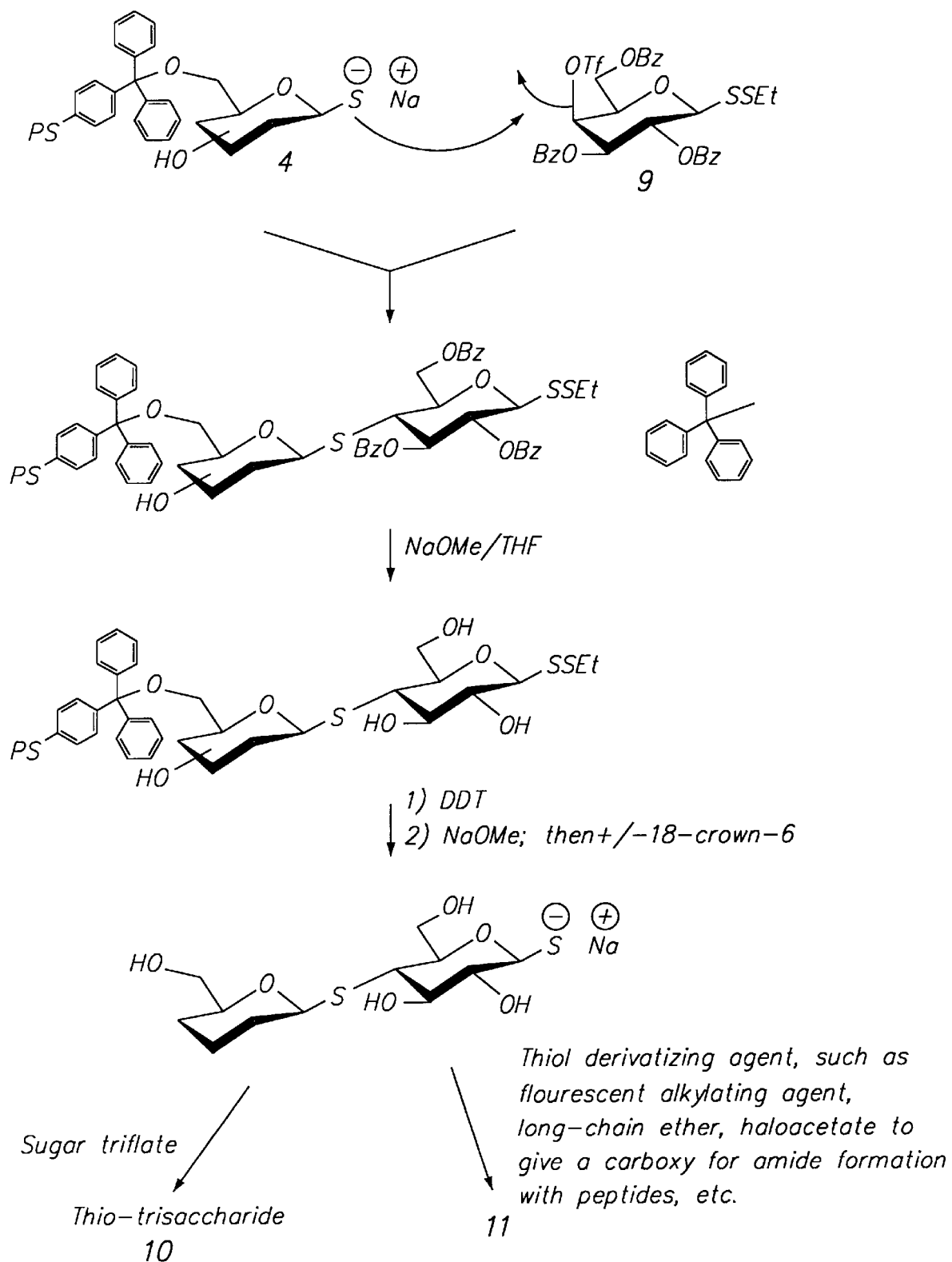
FIG. 4 illustrates a second reaction scheme for the formation of an immobilized saccharide group with a second saccharide group having a nucleophilic displaceable group thereon. In the bound saccharide group depicted in this figure, the hydroxyl groups are unprotected and in the unbound saccharide, the hydroxyl groups at the 2, 3 and 6 positions are protected and this saccharide further comprises a protected thiol group at the anomeric carbon atom thereof (PS in this figure refers to polystyrene).

The methods of the invention are not limited to a single saccharide or oligosaccharide addition reaction but, by selection of the suitable second saccharide or oligosaccharide, can result in numerous addition reactions as illustrated in FIG. 4. Specifically, if the saccharide added to the immobilized saccharide or oligosaccharide itself contains a protected thiol (e.g., compound 9, FIG. 4), the reaction can be repeated to produce longer oligosaccharides such as a trisaccharide (compound 10, FIG. 4).

Further, the final oligosaccharide can, prior to cleavage from the solid support, be labeled with groups commonly used to confer utility to oligosaccharides and thio-oligosaccharides (11), such as fluorescent tags (dansyl, rhodamine etc), biotin, radiolabeled species, lipids for micelle formation, structures to enhance cell-uptake, and the like. This is especially useful when the resultant product is intended to be used in enzyme inhibition studies, cell binding studies, targeting studies and the like.

The following examples illustrate typical reaction scheme, of this invention and are not to be construed in any way as limiting the scope of this invention. Those skilled in the art will recognize suitable alternative materials and conditions by which the object of this invention may be achieved. Unless otherwise stated, all temperatures are in degrees Celsius.

EXAMPLES

In the examples below, the following abbreviations have the following meanings. If an abbreviation is not defined, it has its generally accepted meaning.

| | | |
|---|---|---|
| Å | = | angstroms |
| bd | = | broad doublet |
| bs | = | broad singlet |
| d | = | doublet |
| dd | = | doublet of doublets |
| ddd | = | doublet of doublet of doublets |
| DMAP | = | dimethylaminopyridine |
| DTT | = | dithiothreitol |
| DVB | = | divinylbenzene |
| g | = | grams |
| h | = | hour |
| L | = | liter |
| m | = | multiplet |
| M | = | molar |
| mg | = | milligram |
| min | = | minute |
| mL | = | milliliter |
| mmol | = | millimole |
| q | = | quartet |
| s | = | singlet |
| t | = | triplet |
| TFA | = | trifluoroacetic acid |
| THF | = | tetrahydrofuran |
| µL | = | microliter |
| µmol | = | micromole |

Solid Phase Synthesis of Thio-Oligosaccharides

The following series of reactions shows the step-by-step formation of a sulfur-linked sugar, including formation of the starting reactants. The reactions are illustrated for four separate compounds. Those skilled in the art will be able to form other compounds using these examples and modifying reaction conditions as appropriate for selected reagents and desired end products.

1. Protection of a Free Thiol as an Unsymmetrical Disulfide:

Formation of the following compounds is illustrated below:

Ethyl 2,3,4,6-tetra-O-acetyl-1-dithio-β-D-galactopyranoside (A-1);

Ethyl 2,3,4,6-tetra-O-acetyl-1-dithio-β-D-glucopyrano side, (A-2);

Ethyl 2-acetamido-3,4,6-tri-O-acetyl-2-deoxy-1-dithio-β-D-glucopyranoside (A-3); and Methyl 5-acetamido-4,7,8,9-tetra-O-acetyl-3,5,-dideoxy-D-glycero-α-D-galacto-2-nonulopyranosylonate-dithioethyl (A-4).

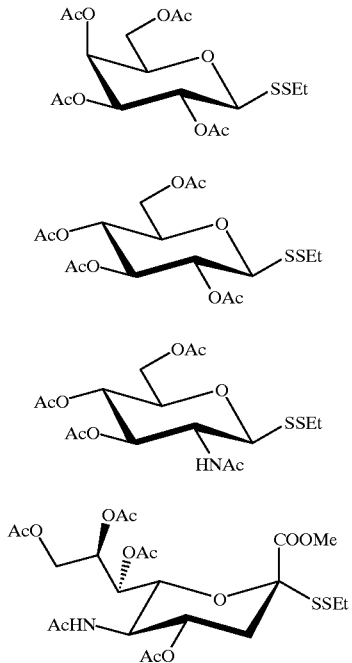

A. Preparation of Compound A-1:

2,3,4,6-Tetra-O-acetyl-1-thio S-acetyl -β-D-galactopyranoside (B. Rajanikanth et al., *Tetrahedron Lett.*, 28:20, pp. 2295–2296 (1987))(557 mg, 1.37 mmol) was dissolved in a mixture of methanol (15 mL) and dichloromethane (5 mL). After cooling to −40° C., methanolic sodium methoxide (1.5 mL, 1.5 mmol) was added. After 1 h at −40° C., ion exchange resin [IR-120 (H+ form)] was added and the reaction mixture was allowed to warm to room temperature. After filtration, the filtrate was evaporated in vacuo. The residue was dissolved in dichloromethane (14 mL) and diethyl-N-ethyl-sulfenylhydrazodicarboxylate (360 mg, 2.0 mmol) was added and stirred at room temperature. After 10 min, the solution was concentrated to provide a residue which was purified by column chromatography (SiO$_2$, hexane/ethyl acetate 2:1) to provide for compound A-1 (580 mg, 100%) as a colorless amorphous mass. Rf=0.27 (hexane/ethyl acetate 2:1).

$^1$H-NMR (360-MHz, CDCl$_3$):δ=1.30 (dd, 3 H, J=7.4 Hz, CH$_3$), 1.96, 2.02, 2.03, 2.13 (4 s, 12 H, 4 COCH$_3$), 2.79 (ddd, 2 H, J=7.0 Hz, J=7.4, J=1.3, SCH$_2$), 3.94 (ddd, 1 H, J$_{4,5}$=1.0 Hz, J$_{5,6a}$=6.6, J$_{5,6}$=7.6, 5-H), 4.10 (ddd, 2 H 6a-H, 6b-H), 4.51 (d, 1 H, J$_{1,2}$=10.0 Hz, 1-H), 5.05 (dd, 1 H, J$_{2,3}$=10.0 Hz, J$_{3,4}$=3.30 Hz, 3-H), 5.38 (dd, 1 H, J$_{1,2}$=10.0 Hz, J$_{2,3}$=10.0, 2-H), 5.40 (dd, 1 H, J$_{3,4}$=3.3 Hz, J$_{4,5}$=1.0, 4-H); m/z calc. for C$_{16}$H$_{24}$O$_9$S$_2$(M+Na) 447.1 found 447.0.

C$_{16}$H$_{24}$O$_9$S$_2$ (424.49)

B. Preparation of Compound A-2

Compound A-2 was prepared from 2,3,4,6-tetra-O-acetyl-1-thio-S-acetyl-β-D-glucopyranoside (J. Defaye et al., *Carbohydr. Res.*, 130:317–321 (1984)) according to the method used in preparation of compound A-1.

$^1$H-NMR (360-MHz, CDCl$_3$):δ=1.28 (t, 3 H, J=7.36 Hz, CH$_3$), 1.98, 2.00, 2.01, 2.04 (4 s, 12 H, 4 COCH$_3$), 2.77 (m, 2 H, SCH$_2$), 3.70 (m, 1 H, 5-H), 4.12 (dd, 1 H, J$_{5,6}$=2.5 Hz, J$_{6,6}$=12.4, 6-H$_a$), 4.19 (dd, J$_{5,6}$=4.8 Hz, J$_{6,6}$=12.4, 6-H$_b$), 4.49 (m, 1 H, 1-H), 5.07 (m, 1 H, 2-H), 5.21 (m, 2 H, 3-H, 4-H).

C$_{16}$H$_{24}$O$_9$S$_2$ (424.49)

C. Preparation of Compound A-3:

Compound A-3 was prepared from 2-acetamido-3,4,6-tri-O-acetyl-2-deoxy-1-thio-S-acetyl-β-D-glucopyranoside (D. Zanini et al., *Tetrahedron Lett.*, 36:41, pp. 7383–7386 (1995)) according to the method used in preparation of compound A-1.

$^1$NMR (360 MHz, CDCl$_3$):δ1.29 (t, 3 H, J=7.3 Hz, CH$_3$), 1.92, 2.01, 2.02, 2.05 (4 s, 12 H, 4 COCH$_3$), 2.79 (q, 2 H, J=7.3 Hz, SCH$_2$), 3.71 (m, 1 H), 4.16 (m, 3 H), 5.06, 5.26 (2 dd, 2 H, J=10.3 Hz, J=9.7), 5.54 (d, 1 H, J=5.5 Hz, NH).

C$_{16}$H$_{25}$O$_8$NS$_2$ (423.51)

D. Preparation of Compound A-4:

Compound A-4 was prepared from methyl 5-acetamido-4,7,8,9-tetra-O-acetyl-3,5,-dideoxy-2-thio-S-acetyl-D-glycero-α-D-galacto-2-nonulopyranosylonate (A. Hasegawa et al., *J. Carbohydr. Chem.*, 5:11–19 (1986)) according to the method used in preparation of compound A-1.

$^1$NMR (360 MHz, CDCl$_3$):δ=1.30 (t, 3 H, J=7.3 Hz, CH$_3$), 1.87, 2.03, 2.04, 2.11, 2.12 (5 s, 15 H, 5 COCH$_3$), 2.25 (dd, 1 H, 3-H$_e$), 2.80 (m, 2 H, SCH$_2$), 3.79 (s, 3 H, COOMe), 3.89–4.19 (m, 3 H, 5-H, 6-H, 9a-H), 4.36 (m, 1 H, 9-H$_b$), 4.87 (m, 1 H, 4-H), 5.15 (d, 1 H, J=8.9 Hz, NH), 5.29 (m, 2 H, 7-H, 8-H).

C$_{22}$H$_{33}$O$_{12}$NS$_2$ (567.64)

2. Deacetylation of A-1, A-2, A-3, A-4:

Formation of the following compounds is illustrated below:

Ethyl 1-dithio-β-D-galactopyranoside (1a);

Ethyl 1-dithio-β-D-glucopyranoside (1b);

Ethyl 2-acetamido-2-deoxy-1-dithio-β-D-glucopyranoside (1c); and

Methyl-5-acetamido-3,5,-dideoxy-D-glycero-β-D-galacto-2-nonulopyranosylonate-dithioethyl (1d).

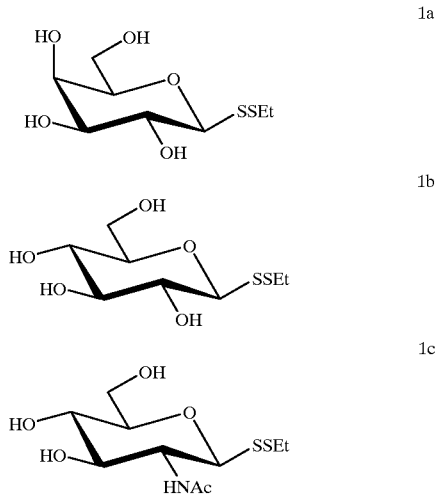

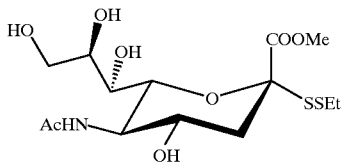

1d

A. Preparation of Compound 1a:

Compound A-1 (500 mg, 1.18 mmol) was dissolved in dry methanol (10 mL) and treated with methanolic sodium methoxide (1 M, 150 µL). After 4 h, the solution was neutralized with Amberlite IR-120 (H$^+$) resin, filtered and concentrated. Compound 1a was obtained as a colorless amorphous mass (300 mg, 100%).

Rf=0.35 (dichloromethane/methanol 5:1);

$^1$NMR (360 MHz, CD$_3$OD):δ=1.30 (t, 3 H, J=7.34 Hz, CH$_3$), 2.83 (m, 2 H, SCH$_2$), 3.49 (dd, 1 H, J$_{5,6}$=3.3 Hz, J$_{6,6}$=9.3, 6-H$_a$), 3.51–3.71 (m, 3 H, 3-H, 5-H, 6-H$_b$), 3.75 (dd, 1 H, J$_{1,2}$=9.6Hz, J$_{2,3}$=9.4, 2-H), 3.88 (m, 1 H, 4-H), 4.31 (d, 1 H, J$_{1,2}$=9.6 Hz, 1-H).

C$_8$H$_{16}$O$_5$S$_2$ (256.34)

B. Preparation of Compound 1b:

Compound 1b was prepared in accordance with the method of preparation of Compound 1a.

$^1$NMR (360 MHz, CD$_3$OD):δ=1.31 (t, 3 H, J=7.34 Hz, CH$_3$), 2.83 (q, 2 H, J=7.4 Hz, SCH$_2$), 3.28–3.41 (m, 3 H), 3.47 (dd, 1 H), 3.64 (mm, 1 H), 3.86 (dd, 1 H, J=1.5 Hz, J=11.5), 4.32 (d, 1 H, J$_{1,2}$=9.4 Hz, 1-H).

C$_8$H$_{16}$O$_5$S$_2$ (256.34)

C. Preparation of Compound 1c:

Compound 1c was prepared in accordance with the method of preparation of Compound 1a.

$^1$H-NMR (360-MHz, CD$_3$OD):δ=1.28 (t, 3 H, CH$_3$), 1.95 (s, 3 H, NCOCH$_3$), 2.82 (m, 2 H, SCH$_2$), 3.26–3.35 (m, 2 H, 4-H, 5-H), 3.46 (dd, 1 H, J$_{2,3}$=10.2 Hz, J$_{2,3}$=8.5, 3-H), 3.66 (dd, 1 H, J$_{5,6}$=5.3 Hz, J$_{6,6}$=12.0, 6-H$_a$), 3.81 (dd, J$_{1,2}$=10.4 Hz, J$_{2,3}$=10.2, 2-H), 3.86 (dd, J$_{5,6}$=2.0 Hz, J$_{6,6}$=12.0, 6-H$_b$), 4.52 (d, 1 H, J$_{1,2}$=10.4 Hz, 1 -H).

C$_{10}$H$_{19}$NO$_5$S$_2$ (297.40)

D. Preparation of Compound 1d:

Compound 1d was prepared in accordance with the method of preparation of Compound 1a.

$^1$NMR (360 MHz, CD$_3$OD):δ=1.28 (t, 3 H, J=7.4 Hz, CH$_3$), 2.76 (m, 1 H, 3-H$_a$), 2.81 (m, 2 H, SCH$_2$), 3.47–3.83 (m, 7 H, 4-H, 5-H, 6-H, 7-H, 8-H, 9-H), 3.83 (s, 3 H, COOCH$_3$).

C$_{14}$H$_{21}$NO$_8$S$_2$ (395.46)

3. Coupling of 1a, 1b, 1c, 1d to solid support (example—trityl chloride resin):

Formation of the following compounds is illustrated below:

Ethyl 1-dithio-6-trityl-polymer-β-D-galactopyranoside (2a);

Ethyl 1-dithio-6-trityl-polymer-β-D-glucopyranoside (2b);

Ethyl 2-acetamido-2-deoxy-1-dithio-6-trityl-polymer-β-D-glucopyranoside (2c); and Methyl 5-acetamido-2-dithio-3,5-dideoxy-6-trityl-polymer D-glycero-β-D-galacto-2-nonulopyranosylonate (2d).

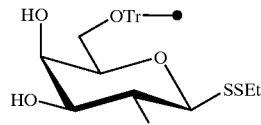

2a

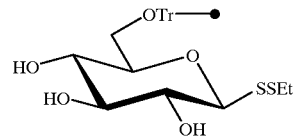

2b

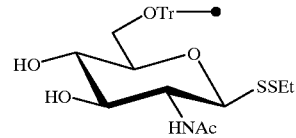

2c

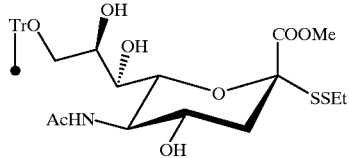

2d

A. Preparation of Compound 2a:

Compound 1a (200 mg, 780 µmol) was dissolved in dry pyridine (8 mL). Tritylchloride-resin (1g, 950 mmol trityl chloride resin, loading 0.95 mmol/g of active chlorine, polymer matrix:copolystyrene, 1% DVB, 200–400 mesh, Novabiochem) and DMAP (5 mg) were added, and the mixture was heated for 24 h at 60° C. After cooling to room temperature, methanol (500 µL) was added and, after 1h, the resin was filtered off, washed successively with N,N-dimethylformamide, methanol, tetrahydrofuran and dichloromethane (10 mL each, the whole cycle repeated twice) and dried under high vacuum. The loading of the sugar to the resin was determined by elemental analysis (sulfur content) and was 0.43 mmol/g.

B–D. Preparation of Compounds 2b, 2c, 2d:

Compounds 2b—2d were prepared in accordance with the method of preparation of Compound 2a.

4. Generating the Free Thiol on the Resin:

Formation of the following compounds is illustrated below:

1-Thio-6-trityl-polymer-β-D-galactopyranoside (3a);

1-Thio-6-trityl-polymer-β-D-glucopyranoside (3b);

2-acetamido-2-deoxy-1-thio-6-trityl-polymer-β-D-glucopyranoside (3c); and

Methyl 5-acetamido-3,5,-dideoxy-2-thio-6-trityl-polymer-D-glycero-α-D-galacto-2-nonulopyranosylonate (3d):

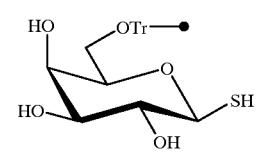

3a

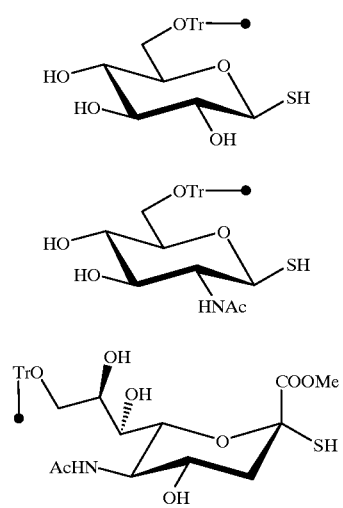

A. Preparation of Compound 3a:

The resin 2a (50 mg) was swollen in dry tetrahydrofuran (2 mL). Dry methanol (300 μL), dithiothreitol (74 mg) and triethylamine (180 μL) were added and the mixture was shaken for 10 h at room temperature. The resin was filtered off and washed successively with N,N-dimethylformamide, methanol, tetrahydrofuran and dichloromethane (2 mL each, the whole cycle repeated twice) and dried under high vacuum.

IR (of beads):SH stretch:2565 cm$^{-1}$.

B–D. Preparation of Compounds 3b, 3c, 3d:

Compounds 3b—3d were prepared in accordance with the method of preparation of Compound 3a.

5. Generating the Sodium-thiolate on the Resin:

Formation of the following compounds is illustrated below:

1-Sodiumthiolate-6-trityl-polymer-β-D-galactopyranoside (4a);

1-Sodiumthiolate-6-trityl-polymer-β-D-glucopyranoside (4b);

1-Sodiumthiolate-6-trityl-polymer-2-acetamido-2-deoxy-β-D-glucopyranoside (4c); and Methyl 5-acetamido-3,5,-dideoxy-2-sodiumthiolate-9-trityl-polymer-D-glycero-α-D-galacto-2-nonulopyranosylonate (4d).

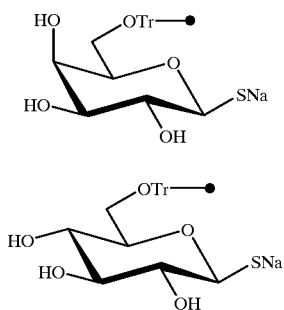

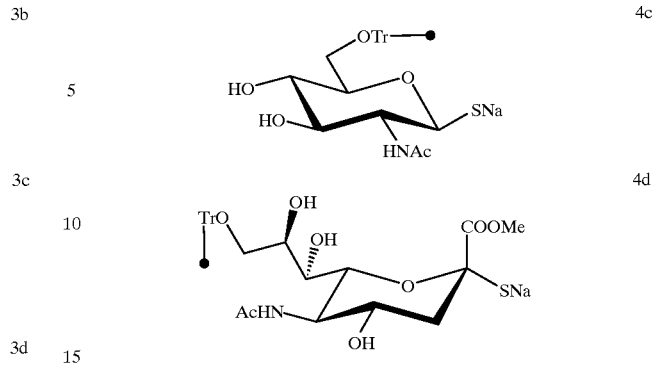

A. Preparation of Compound 4a:

The resin 3a (50 mg) was swollen in tetrahydrofuran (2 mL) for 10 min.

Methanolic sodium methoxide (1 M, 150 μL) was added and the resin was shaken at room temperature. After 2 h, the resin was filtered off and washed successively with N,N-dimethylformamide, methanol, tetrahydrofuran and dichloromethane (2 mL each, the whole cycle repeated twice) and dried under high vacuum.

B–D. Preparation of Compounds 4b, 4c, 4d:

Compounds 4b—4d were prepared in accordance with the method of preparation of Compound 4a.

6. Reaction of the Immobilized Carbohydrate Sodium Thiolates with Derivatives Having a Leaving Group A. Example with of 1,2,3,4-Di-isopropylidene-6-O-trifluoromethanesulfono-α-D-galactopyranoside Formation of the following compounds is illustrated below:

Isopropyl O-β-D-galactopyranosyl-(1→6)-2,3,4-tri-O-isopropylidene-β-D-galactopyranoside (5-B-C-1);

Isopropyl O-β-D-glucopyranosyl-(1→6)-2,3,4-tri-O-isoprolpylidene-β-D-galactopyranoside (5-B-C-2);

Isopropyl O-β-D-2-acetamido-2-deoxy-β-D-glucopyranosyl-( 1→6)-2,3,4-tri-O-isopropylidene-β-D-galactopyranoside (5-B-C-3); and Isopropyl O-(5-acetamido-3,5-dideoxy-D-glycero-(α-D-galacto-2-nonulopyranosylonate-(2→6)-2,3,4-tri-O-isopropylidene-β-D-galactopyranoside (5-B-C-4).

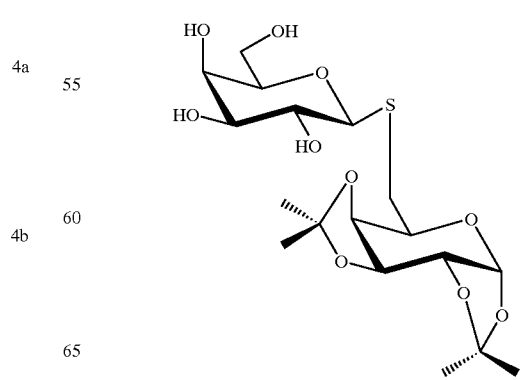

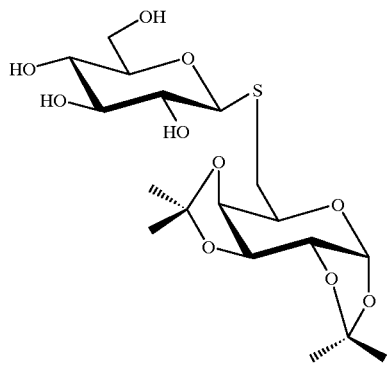

5-B-C-2

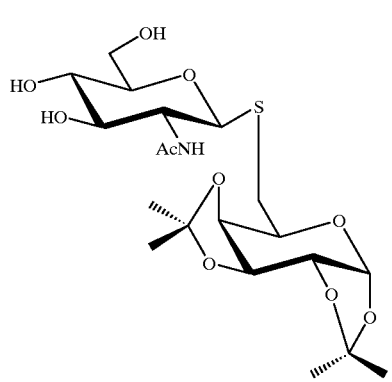

5-B-C-3

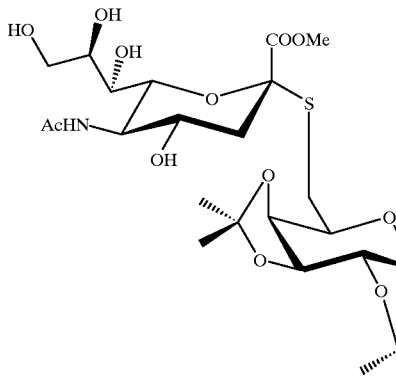

5-B-C-4 a. Preparation of Compound 5-B-C-1:

The resin 4a (50 mg) was swollen in THF (1 mL) for 10 min. The crown ether 15-crown-5 (3 drops) and 1,2,3,4-di-isopropylidene-6-O-trifluoromethanesulfono-α-D-galactopyranoside (50 mg) were added, and the mixture was shaken at room temperature for 10 h. The resin was filtered off and washed successively with N,N-dimethylformamide, methanol, tetrahydrofuran and dichloromethane (2 mL each, the whole cycle repeated twice). The resin was treated with 2% TFA in dichloromethane for 10 min. After filtration, toluene was added and the filtrate was concentrated and evaporated twice with toluene. After column chromatography (SiO$_2$, dichloromethane/methanol 9:1) compound 5-B-C-1 was obtained.

$^1$NMR (360 MHZ, CD$_3$OD):δ=1.32, 1.34, 1.39, 1.51 (4 s, 12 H, 4 CH$_3$), 2.84 (dd, 1 H, J$_{5,6}$=7.4 Hz, J$_{6,6}$=13.7, 6a-Ha), 2.92 (dd, 1 H, J$_{5,6}$=6.6 Hz, J$_{6,6}$=13.7, 6a-H$_b$), 3.27–3.88 (m, 5 H, 2b-H, 3b-H, 4b-H, 5b-H, 6b-H), 3.96 (m, 1 H, 5a-H), 4.33 (dd, 1 H, J$_{1,2}$=5.4Hz, J$_{2,3}$=2.4, 2a-H), 4.35 (d, 1 H, J$_{1,2}$=9.7 Hz, 1 b-H), 4.46 (dd, 1 H, J$_{3,4}$=7.9 Hz, J$_{4,5}$=1.8, 4A-H), 4.62 (dd, 1 H, J$_{2,3}$=2.4 Hz, J$_{3,4}$=7.9, 3a-H), 5.45 (d, 1 H, J$_{1,2}$=5.0 Hz, 1 a-H).

C$_{18}$H$_{30}$O$_{10}$S (438.49)

b. Preparation of Compound 5-B-C-2:

Compound 5-B-C-2 was prepared in accordance with the method of preparing Compound 5-B-C-1.

$^1$H-NMR (360-MHz, CD$_3$OD):δ=1.32, 1.34, 1.40, 1.51 (4 s, 12 H, 4 CH$_3$), 2.83 (dd, 1 H, J$_{5,6}$=7.5 Hz, J$_{6,6}$=13.7, 6a-H$_a$), 2.92 (dd, 1 H, J$_{5,6}$=6.5 Hz, J$_{6,6}$=13.7, 6a-H$_b$), 3.19 ( dd, 1 H, J$_{1,2}$=9.6 Hz, J$_{2,3}$=8.6, 2b-H), 2.25–3.35 (m, 3 H, 3b-H, 6b-H), 3.65 (m, 1 H, 4b-H), 3.85 (m, 1 H, 5b-H), 3.96 (m, 1 H, 5a-H), 4.33 (dd, 1 H, J$_{1,2}$=54 Hz, J$_{2,3}$=2.4, 2a-H), 4.40 (d, 1 H, J$_{1,2}$=9.6 Hz, 1b-H), 4.48 (dd, 1 H, J$_{3,4}$=7.9 Hz, J$_{4,5}$=1.8, 4a-H), 4.63 (dd, 1 H, J$_{2,3}$=2.4 Hz, J$_{3,4}$=7.9, 3a-H), 5.45 (d, 1 H, J$_{1,2}$=5.0 Hz, 1a-H).

C$_{18}$H$_{30}$O$_{10}$S (438.49)

c. Preparation of Compound 5-B-C-3:

Compound 5-B-C-3 was prepared in accordance with the method of preparing Compound 5-B-C-1.

$^1$H-NMR (360-MHz, CD$_3$OD):δ=1.32, 1.33, 1.39, 1.51 (4 s, 12 H, 4 CH$_3$), 1.97 (s, 3 H, NCOCH$_3$), 2.78 ( dd, 1 H, J$_{5,6}$=6.3 Hz, J$_{6,6}$=13.6, 6a-H$_b$),2.94 (dd, 1 H, J$_{5,6}$=6.3 Hz, J$_{6,6}$=13.6, 6a-H$_a$), 3.29 (m, 1 H, 4b-H), 3.432 (dd, 1 H, J$_{2,3}$=9.7 Hz, J$_{3,4}$=8.4, 3b-H), 3.65 (m, 2 H, 5b-H, 6b-H$_a$), 3.73 (dd, 1 H, J$_{1,2}$=10.3 Hz, J$_{2,3}$=9.7, 2b-H), 3.86 (dd, 1 H, J$_{5,6}$=2.0 Hz, J$_{6,6}$=12.0, 6b-H$_b$), 3.93 (m, 1 H, 5a-H), 4.32 (dd, 1 H, J$_{1,2}$=5.0 Hz, J$_{2,3}$=2.4, 2a-H), 4.38 (dd, 1 H, J$_{3,4}$=7.9 Hz, J$_{4,5}$=1.8, 4a-H), 4.55 (d, 1 H, J$_{1,2}$=10.3 Hz, 1b-H), 4.62 (dd, 1 H, J$_{2,3}$=2.4 Hz, J$_{3,4}$=7.9, 3a-H), 5.45 (d, 1 H, J$_{1,2}$=5.0 Hz, 1a-H).

C$_{20}$H$_{33}$O$_{10}$S (465.53)

d. Preparation of Compound 5-B-C-4:

Compound 5-B-C-4 was prepared in accordance with the method of preparing Compound 5-B-C-1.

$^1$H-NMR (360-MHz, CD$_3$OD):δ=1.31, 1.33, 1.39, 1.49 (4 s, 12 H, 4 CH$_3$), 1.80 (dd, 1 H, J$_{3a,4}$=11.3 Hz, J$_{3a,3c}$=12.8, 3b-H$_a$), 1.98 (s, 3 H, NCOCH$_3$), 2.75 ( dd, 1 H, J$_{3e,4}$=4.6 Hz, J$_{3e,3a}$=12.8, 3b-H$_e$), 2.92 ( m, 2 H, 6a-H), 3.67 (s, 3 H, COOCH$_3$), 3.43–3.86 (m, 8 H, 4b-H, 5a-H, 5b-H, 6b-H, 7b-H, 8b-H, 2 9b-H), 4.23(dd, 1 H, J$_{3,4}$=7.9Hz, J$_{4,5}$=1.9, 4a-H), 4.31 (dd, 1 H, J$_{1,2}$=5.0 Hz, J$_{2,3}$=2.4, 2a-H), 4.61 (dd, 1 H, J$_{2,3}$=2.4 Hz, J$_{3,4}$=7.9, 3a-H), 5.42 (d, 1 H, J$_{1,2}$=5.0 Hz, 1a-H).

C$_{24}$H$_{39}$O$_{13}$S (567.62)

B. Example with n-Octyl 2,3,6-tri-O-benzoyl-4-O-trifluoromethane-sulfono-β-D-glucopyranoside Formation of the following compounds is illustrated below:

Octyl O-β-D-galactopyranosyl-(1→4)-β-D-galactopyranoside (8-C-1);

Octyl O-β-D-glucopyranosyl-(1→4)-β-D-galactopyranoside (8-C-2);

Octyl O-β-D-2-acetamido-2-deoxy-β-D-glucopyranosyl-(1→4)-β-D-galactopyranoside (8-C-3); and Octyl O-methyl-5-acetamido-3,5-dideoxy-D-glycero-α-D-galacto-2-nonulopyranosylonate-(2→4)-β-D-galactopyranoside (8-C-4).

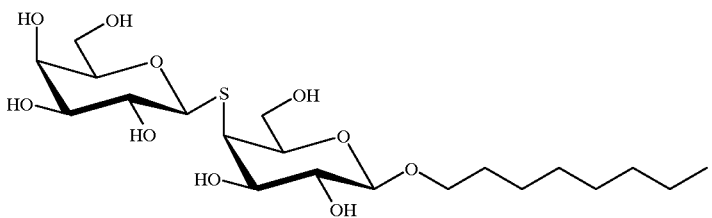

8-C-1

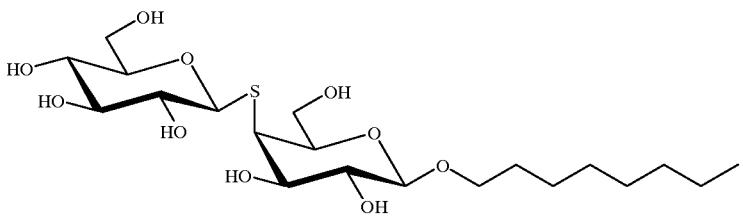

8-C-2

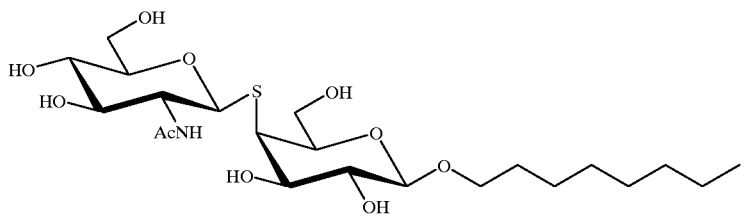

8-C-3

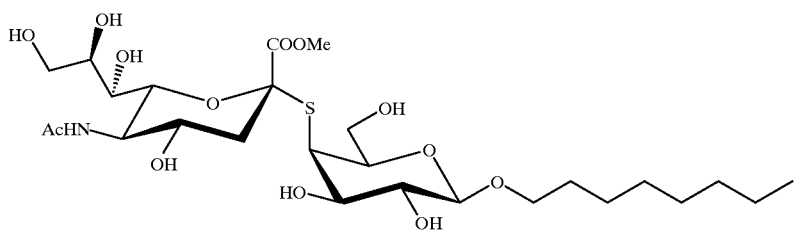

8-C-4 a. Preparation of Compound 8-C-1:

The resin 4a (50 mg) was swollen in tetrahydrofuran (1 mL) for 10 min. The crown ether 15-crown-5 (3 drops) and n-octyl-2,3,6-tri-O-benzoyl-4-O-trifluoromethanesulfono-β-D-glucopyranoside (50 mg) was added, and the mixture was shaken at room temperature for 10 h.

The resin was filtered off and washed successively with N,N-dimethylformamide, methanol, tetrahydrofuran and dichloromethane (2 mL each, the whole cycle repeated twice). The resin was swollen in tetrahydrofuran (2mL) for 10 min., methanolic sodium methoxide (1 M, 300 μL) was added and the resin was shaken at room temperature. After 12 h, the resin was filtered off and washed successively with N,N-dimethylformamide, methanol, tetrahydrofuran and dichloromethane (2 mL each, the whole cycle repeated twice).

The resin was treated with 2% TFA in dichloromethane for 10 min. After filtration, toluene was added and the filtrate was concentrated and evaporated twice with toluene/methanol.

$^1$H-NMR (360-MHz, CD$_3$OD):δ=0.89 (m, 3 H, CH$_3$), 1.29 (m, 10 H, octyl), 1.59 (m, 2 H, OCH$_2$CH$_2$), 3.43–4.02 (m, 14 H, 2 2-H, 2 3-H, 2 4-H, 2 5-H, 2 6-H, OCH$_2$CH$_2$), 4.18 (d, 1 H J$_{1,2}$=7.6 Hz, 1b-H), 4.42 (d, 1 H, J$_{1,2}$ =9.6 Hz, 1a-H).

C$_{20}$H$_{38}$O$_9$S (454.58)

b. Preparation of Compound 8-C-2:

Compound 8-C-2 was prepared in accordance with the method of preparing Compound 8-C-1.

$^1$H-NMR (360-MHz, CD$_3$OD):δ=0.89 (m, 3 H, CH$_3$), 1.28 (m, 10 H, octyl), 1.59 (m, 2 H, OCH$_2$CH$_2$), 3.18–4.02 (m, 14 H, 2 2-H, 2 3-H, 2 4-H, 2 5-H, 2 6-H, OCH$_2$CH$_2$), 4.18 (d, 1 H, J$_{1,2}$=7.6 Hz, 1a-H), 4.48 (d, 1 H, J$_{1,2}$=9.7 Hz, 1b-H).

C$_{20}$H$_{38}$O$_9$S (454.58)

c. Preparation of Compound 8-C-3:

Compound 8-C-3 was prepared in accordance with the method of preparing Compound 8-C-1.

$^1$H-NMR (360-MHz, CD$_3$OD):δ=0.89 (m, 3 H, CH$_3$), 1.2.9 (m, 10 H, octyl), 1.57 (m, 2 H, OCH$_2$CH$_2$), 1.99 (s, 3 H, NCOCH$_3$), 3.26–3.98 (m, 14 H, 2 2-H, 2 3-H, 2 4-H, 2 5-H, 2 6-H, OCH$_2$CH$_2$),4.16 (d, 1 H, J$_{1,2}$=7.6 Hz, 1a-H), 4.70 (d, 1 H, J$_{1,2}$=10.4 Hz, 1b-H).

C$_{22}$H$_{41}$NO$_9$S (495.63)

d. Preparation of Compound 8-C-4:

Compound 8-C-4 was prepared in accordance with the method of preparing Compound 8-C-1.

$^1$H-NMR (360-MHz, CD$_3$OD):δ=0.88 (m, 3 H, CH$_3$), 1.28 (m, 10 H, octyl), 1.56 (m, 2 H, OCH$_2$CH$_2$), 1.99 (s, 3 H, NCOCH$_3$), 1.79 (dd, 1 H, J$_{3a,4}$ =11.3 Hz, J$_{3a,3e}$=12.8, 3b-H$_a$), 1.97 (s, 3 H, NCOCH$_3$), 2.75 ( dd, 1 H, J$_{3e,4}$=4.6 Hz, J$_{3e,3a}$=12.8, 3b-H$_e$), 3.67 (s, 3 H, COOCH$_3$), 3.20–4.00 (m, 15 H, 2a-H, 3A-H, 2 4-H, 2 5-H, 3 6-H, 7b-H, 8b-H, 2 9b-H, OCH$_2$CH$_2$),4.20 (d, 1 H, J$_{1,2}$=7.6 Hz, 1a-H).

C$_{26}$H$_{47}$NO$_{13}$S (613.73)

7. Preparation of 8-Methoxycarbonyloctyl O-⊖-D-galactopyranosyl-(1→4)-2,3-di-O-acetyl-6-O-benzoyl-β-D-glucopyranoside (6-A-C)

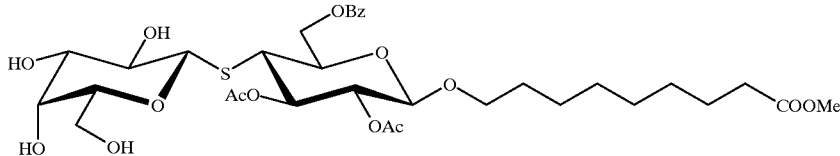

The resin 4a (50 mg) was swollen in tetrahydrofuran (1 ml,) for 10 min. The crown ether 15-crown-5 (3 drops) and 8-methoxycarbonyloctyl n-octyl-2,3-di-O-acetyl-6-O-benzoyl-4-O-trifluoromethanesulfono-β-D-glucopyranoside 5-A (50 mg) were added, and the mixture was shaken at room temperature for 10 h.

The resin was filtered off and washed successively with N,N-dimethylformamide, methanol, tetrahydrofuran and dichloromethane (2 mL each, the whole cycle repeated twice). The resin was treated with 2% TF-A in dichloromethane for 10 min. After filtration, toluene was added and the filtrate was concentrated and evaporated twice with toluene/methanol. The residue was purified on $SiO_2$ [dichloromethane/methanol (15:1→12:1)] to give the title compound 6-A-C.

$^1$H-NMR (360-MHz, $CD_3OD$):δ=1.17 (m, 8 H, 4 $CH_2$), 1.49 (m, 4 H, 2 $CH_2$), 1.97, 2.05 (2 s, 6 H, 2 $CH_3CO$), 2.26 (dd, 1 H, $J_{3,4}$=11.1 Hz, $J_{4,5}$=11.1, 4a-H), 3.28–3.85 (m, 8 H, 2b-H, 3b-H, 4b-H, 5b-H, 6b-H, $OCH_2$), 3.58 (s, 3 H, $COOCH_3$), 4.31 (d, 1 H, $J_{1,2}$=9.5 Hz, 1b-H), 4.44 (d, 1 H, $J_{1,2}$=8.0 Hz, 1a-H), 4.51 (dd, 1 H, $J_{5,6}$=6.4 Hz, $J_{6,6}$=12.0, 6a-$H_a$), 4.85 (dd, $J_{1,2}$=8.0 Hz, $J_{2,3}$=9.2, 2a-H), 4.91 (dd, 1 H, $J_{5,6}$=2.1 Hz, $J_{6,6}$=12.0, 6a-$H_b$), 5.08 (dd, $J_{2,3}$=9.2 Hz, $J_{3,4}$=11.1, 3a-H), 7.38, 7.51, 7.96 (m, 5 H, Ph).

$C_{33}H_{48}O_{15}S_2$ (748.85)

8. Preparation of Ethyl 4,6-O-benzylidene-1-dithio-β-D-galactopyranoside 9a

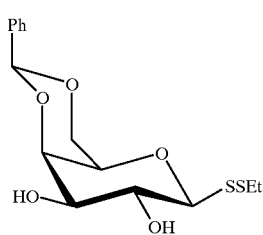

Compound 1a (1.456 g, 5.68 mmol) was suspended in dry acetonitrile (50 mL). Benzaldehyde dimethylacetal (1.3 mL, 8.66 mmol) and p-toluene sulfonic acid (10 mg) were added. After 1 h, triethylamine (0.5 mL) was added, and the clear solution was evaporated in vacuo. The residue was purified on $SiO_2$ [toluene/ethyl acetate (1:1→1:2)] to give the title compound 9a as a colorless amorphous mass, which was crystallized from ethyl acetate/hexane (1.82 g, 93%).

$^1$H-NMR (360-MHz, $CDCl_3$):δ=1.31 (t, 3 H, J=7.4 Hz, $CH_3$), 2.48 (bs, 2 H, OH), 2.83–3.01 (m, 2 H, $SCH_2$), 3.52 (m, 1 H, 5-H), 3.76 (dd, 1 H, $J_{2,3}$=9.1 Hz, $J_{3,4}$=3.6, 3-H), 4.01 (m, 1 H, 6-$H_a$), 4.21–4.27 (m, 3 H, 2-H, 4-H, 6-$H_b$), 4.35 (d, 1 H, $J_{1,2}$=9.1 Hz, 1-H), 5.52 (d, 1 H, CHPh), 7.34–7.49 (m, 5 H, Ph).

$C_{15}H_{20}O_5S_2$ (344.45)

9. Preparation of Ethyl 2,3-di-O-benzoyl-4,6-O-benzylidene-1-dithio-β-D-galactopyranoside 9b.

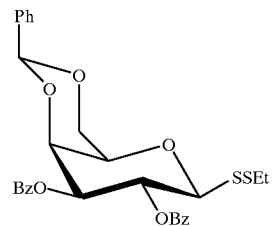

Compound 9a (1.175 g, 3.41 mmol) was dissolved in dry dichloromethane (20 mL) and dry pyridine (2 mL). After cooling to 0° C., benzoyl chloride (1.6 mL, 13.78 mmol) was added. After 2 h, the reaction mixture was diluted with dichloromethane and poured into ice-water. The organic phase was separated and washed with water. The organic layer was dried with magnesium sulfate, filtered and evaporated in vacuo. The residue was purified on $SiO_2$ [hexane/ethyl acetate (4:1→5:2)] to give the title compound 9b as a colorless amorphous mass, which was crystallized from ethyl acetate/hexane (1.72 g, 91%).

$^1$H-NMR (360-MHz, $CDCl_3$):δ=1.24 (t, 3 H, J=7.4 Hz, $CH_3$), 2.85–2.97 (m, 2 H, $SCH_2$), 3.73 (m, 1 H, 5-H), 4.07 (dd, 1 H, $J_{5,6}$=1.6 Hz, $J_{6,6}$=12.4, 6-$H_a$), 4.34 (dd, 1 H, $J_{5,6}$=1.6 Hz, $J_{6,6}$=12.4, 6-$H_b$), 4.61 (m, 1 H, 4-H), 4.78 (d 1 H, $J_{1,2}$=9.6 Hz, 1-H), 5.41 (dd, 1 H, $J_{2,3}$=10.0 Hz, $J_{3,4}$=3.4, 3-H), 5.52 (d, 1 H, CHPh), 6.27 (dd, 1 H, $J_{1,2}$=9.6 Hz, $J_{2,3}$=10.0, 2-H), 7.31–7.98 (m, 15 H, 3 Ph).

$C_{29}H_{28}O_7S_2$ (552.67)

10. Preparation of Ethyl 2,3-di-O-benzoyl-1-dithio-β-D-galactopyranoside 9c

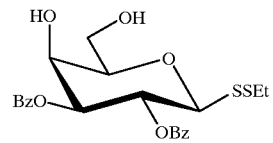

Compound 9b (1.5 g, 2.71 mmol) was dissolved in dry dichloromethane (40 mL). Ethanethiol (1.5 mL, 78.2 mmol) and p-toluenesulfonic acid (30 mg) were added. After 1 h stirring at room temperature, triethylamine (0.5 mL) was added and the reaction mixture was evaporated in vacuo. The residue was purified on $SiO_2$ [toluene/ethyl acetate (3:1→2:1)]. Compound 9c was obtained as a colorless amorphous mass, which was crystallized from ethyl acetate/hexane (1.13 g, 90%).

$^1$H-NMR (360-MHz, CDCl$_3$):δ=1.26 (t, 3 H, =7.3 Hz, CH$_3$), 1.95 (bs, 2 H, OH), 2.79 (q, 2 H, J=7.3 Hz, SCH$_2$), 3.85 (m, 1 H, 5-H), 3.96 (m, 2 H, 6-H), 4.42 (m, 1 H, 4-H), 4.75 (d, 1 H, J$_{1,2}$=9.8 Hz, 1-H), 5.34 (dd, 1 H, J$_{2,3}$=9.9 Hz, J$_{3,4}$=3.0, 3-H), 5.99 (dd, 1 H, J$_{1,2}$=9.8 Hz, J$_{2,3}$=9.9, 2-H), 7.33–7.97 (m, 10 H, 2 Ph).

C$_{22}$H$_{24}$O$_7$S$_2$ (464.56)

11. Preparation of Ethyl 2.3.6-tri-O-benzoyl-1-dithio-β-D-galactopyranoside 9d

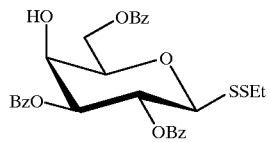

Compound 9c (800 mg, 1.72 mmol) was dissolved in dry dichloromethane (20 mL) and dry pyridine (1.8 mL). After cooling to −40° C., benzoyl chloride (220 μL, 1.89 mmol) was added. After 2 h at −40° C., methanol was added (200 μL) and the reaction mixture was diluted with dichloromethane and poured into ice water. The organic phase was separated and washed with water. The organic layer was dried with magnesium sulfate, filtered and evaporated in vacuo. The residue was purified on SiO$_2$ [hexane/ethyl acetate (4:1→3:1)] to give the title compound 9d as a colorless amorphous mass, which was crystallized from ethyl acelate/hexane (871 mg, 89%).

$^1$H-NMR (360-MHz, CDCl$_3$):δ=1.24 (t, 3 H, J=7.3 Hz, CH$_3$), 2.49 (bd, 1 H, 4-OH), 2.80 (q, 2 H, J=7.3 Hz, SCH$_2$), 4.12 (m, 1 H, 5-H), 4.38 (m, 1 H, 4-H), 4.58 (dd, 1 H, J$_{5,6}$=6.2 Hz, J$_{6,6}$=11.5, 6-H$_a$), 4.64 (dd, 1 H, J$_{5,6}$=6.2 Hz, J$_{6,6}$=11.5, 6-H$_b$), 4.77 (d, 1 H, J$_{1,2}$=9.9 Hz, 1-H), 5.40 (dd, 1 H, J$_{2,3}$=9.9 Hz, J$_{3,4}$=3.1, 3-H), 5.98 (dd, 1 H, J$_{1,2}$=9.9 Hz, J$_{2,3}$=9.9, 2-H), 7.33–8.05 (m, 15 H, 3 Ph).

C$_{29}$H$_{28}$O$_8$S$_2$ (568.67)

12. Preparation of Ethyl 2,3,6-tri-O-benzoyl-1-dithio-4-O-trifluoromethanesulfono-β-D-galactopyranoside 9e

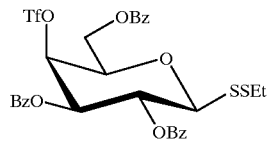

Compound 9d (500 mg, 1.06 mmol) was dissolved in dry dichloromethane (20 mL) and dry pyridine (2.3 mL). After cooling to 0° C., trifluoromethane-sulfonic anhydride (1.6 mL, 9.51 mmol) was added. After 30 min at 0° C. and 1 h at room temperature, the reaction mixture was diluted with dichloromethane (20 ml) and washed with saturated sodium hydrogen carbonate (2 times 10 mL). The organic phase was separated and washed with water. The organic layer was dried with magnesium sulfate, filtered and evaporated in vacuo. The solid residue was used directly without further purification.

13. Preparation of Ethyl 1-dithio-β-D-glucopyranosyl-(1→4)-β-D-glucopyranoside 9A-2-C

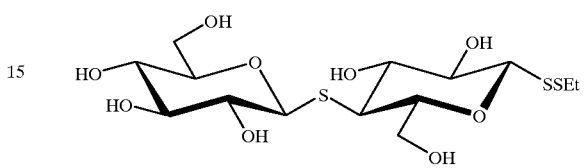

The resin 4b (50 mg) was swollen in tetrahydrofuran (2 mL) for 10 min. The crown ether 15-crown-5 (3 drops) and ethyl 2,3,6-tri-O-benzoyl-1-dithio-O-trifluoromethanesulfono-β-D-galactopyranoside (9) (50 mg) were added, and the mixture was shaken at room temperature for 10 h.

The resin was filtered off and washed successively with N,N-dimethylformamide, methanol, tetrahydrofuran and dichloromethane (2 mL each, the whole cycle repeated twice). The resin was swollen in tetrahydrofuran (2mL) for 10 min., methanolic sodium methoxide (1 M, 300 μL) was added and the resin was shaken at room temperature. After 12 h, the resin was filtered off and washed successively with N,N-dimethylformamide, methanol, tetrahydrofuran and dichloromethane (2 mL each, the whole cycle repeated twice).

The resin was treated with 2% TFA in dichloromethane (1 mL) for 10 min. After filtration the resin was washed with methanol and dichloromethane (2 mL each), then treated again with 2% TFA and washed as described before. Toluene (2 mL) was added and the filtrate was concentrated and evaporated twice with toluene. The residue was dissolved in methanol (2 mL) and passed through a 0.22 μm filter unit (Millipore filter). The filtrate was concentrated and dissolved again in 2 mL of water. Freeze drying gave the title compound 9A-2-C as a colorless amorphous powder.

$^1$H-NMR (360-MHz, CD$_3$OD):δ=1.30 (t, 3 H, J=7.3 Hz, CH$_3$), 2.83 (q, 2 H, J=7.3 Hz SCH$_2$), 3.26–3.89 (m, 12 H, 2 2-H, 2 3-H, 2 4-H, 2 5-H, 2 6-H), 4.31 (d, 1 H, J$_{1,2}$=93Hz, 1b-H), 4.40(d, 1 H, J$_{1,2}$=9.5 Hz, 1a-H).

C$_{14}$H$_{26}$O$_9$S$_3$ (434.55)

14. Preparation of Ethyl 1-dithio-β-D-glucopyranosyl-(1→4)-β-D-glucopyranosyl-(1→4)-β-D-glucopyranoside 10-B

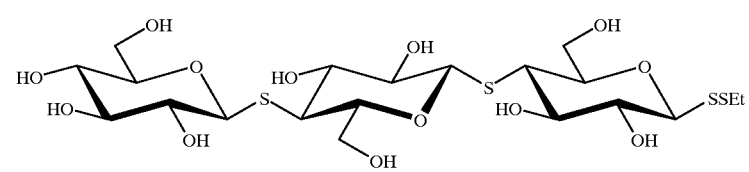

The resin 9A-4 (50 mg) was swollen in tetrahydrofuran (2 mL) for 10 min. The crown ether 15-crown-5 (3 drops) and ethyl 2,3,6-tri-O-benzoyl-1-dithio-O-trifluoromethanesulfono-β-D-galactopyranoside (9) (50 mg) were added, and the mixture was shaken at room temperature for 10 h.

The resin was filtered off and washed successively with N,N-dimethylformamide, methanol, tetrahydrofuran and dichloromethane (2 mL each, the whole cycle repeated twice). The resin was swollen in tetrahydrofuran (2 mL) for 10 min., methanolic sodium methoxide (1 M, 300 μL) was added and the resin was shaken at room temperature. After 12 h, the resin was filtered off and washed successively with N,N-dimethylformamide, methanol, tetrahydrofuran and dichloromethane (2 mL each, the whole cycle repeated twice). The resin was treated with 2% TFA in dichloromethane (1 mL) for 10 min. After filtration the resin was washed with methanol and dichloromethane (2 mL each), then treated again with 2% TFA and washed as described before. Toluene (2 mL) was added and the filtrate was concentrated and evaporated twice with toluene. The residue was dissolved in methanol (2 mL) and passed through a 0.22 μm filter unit (Millipore filter). The filtrate was concentrated and dissolved again in 2 mL of water. Freeze drying yielded the title compound 10-B as a colorless amorphous powder.

$^1$H-NMR (360-MHz, CD$_3$OD): δ=1.30 (t, 3 H, J=7.3 Hz, CH$_3$), 2.83 (q, 2 H, J=7.3 Hz SCH$_2$), 3.26–3.87 (m, 18 H, 3 2-H, 3 3-H, 3 4-H, 3 5-H, 3 6-H), 4.31 (d, 2 H, J$_{1,2}$=9.3 Hz, 1b-H, 1c-H), 4.40 (d, 1 H, J$_{1,2}$=9.5 Hz, 1a-H).

C$_{20}$H$_{35}$O$_{12}$S$_4$ (595.76)

From the foregoing description, various modifications and changes in the composition and method will occur to those skilled in the art. All such modifications coming within the scope of the appended claims are intended to be included therein.

What is claimed is:

1. A method for forming a sulfur-linked di- or oligosaccharide on a solid support which method comprises:
   i) immobilizing a first saccharide or oligosaccharide on a solid support wherein the first saccharide or oligosaccharide comprises a protected thiol group of the formula —SR at the anomeric carbon atom of the reducing saccharide unit wherein R is a thiol group protecting agent;
   ii) deprotecting the thiol group and optionally converting the deprotected thiol group to the corresponding thiolate;
   iii) optionally adding a metal complexing agent; and
   iv) contacting the immobilized saccharide or oligosaccharide group formed in ii) or iii) above with a second saccharide or oligosaccharide comprising a nucleophilic displaceable group in an inert solvent wherein said immobilized saccharide or oligosaccharide forms a solid phase in said solvent and further wherein said contacting is conducted under conditions wherein the thiol or thiolate group displaces said nucleophilic displaceable group thereby forming a sulfide linkage between the first and second saccharides/oligosaccharides.

2. The method of claim 1, wherein each of hydroxyl/amino groups of the second saccharide or oligosaccharide is protected with a removable protecting group.

3. The method of claim 1, wherein the second saccharide or oligosaccharide further comprises a protected thiol group of the formula —SR at the anomeric carbon of the reducing saccharide unit wherein R is a thiol group protecting agent.

4. The method of claim 1, wherein the first saccharide or oligosaccharide immobilized on the solid support is a saccharide or oligosaccharide not protected at any of the hydroxyl/amino groups thereof.

5. The method of claim 1, wherein the solid support is selected from the group consisting of silica, synthetic silicates, biogenic silicates, porous glass, hydrogels, silicate-containing minerals, synthetic polymers, polystyrene, polypropylene, polyethylene glycol, polyacrylamide and copolymers thereof including copolymers of polystyrene and polyethylene glycol and polyacrylamide and polyethylene glycol.

6. The method of claim 1, wherein the thiol-substituted oligosaccharide having a reactive thiol group comprises an oligosaccharide having a reactive thiol group substituent at the anomeric carbon.

7. A method for forming a sulfur-linked di- or oligosaccharide on a solid support which method comprises:
   i) immobilizing a first saccharide or oligosaccharide on a solid support through a cleavable linking arm wherein the first saccharide or oligosaccharide comprises a protected thiol group of the formula —SR at the anomeric carbon of the reducing saccharide unit wherein R is a thiol group protecting agent;
   ii) deprotecting the thiol group and optionally converting the deprotected thiol group to the corresponding thiolate;
   iii) optionally adding a metal complexing agent; and
   iv) contacting the immobilized saccharide or oligosaccharide group formed in ii) or iii) above with a second saccharide or oligosaccharide comprising a nucleophilic displaceable group in an inert solvent wherein said immobilized saccharide or oligosaccharide forms a solid phase in said solvent and further wherein said contacting is conducted under conditions wherein the thiol or thiolate group displaces said nucleophilic displaceable group thereby forming a sulfide linkage between the first and second saccharides/oligosaccharides; and
   v) removing the product produced in iv) from the solid support by cleaving the cleavable linking arm.

8. The method of claim 7, wherein each of the hydroxyl/amino groups of the second saccharide or oligosaccharide is protected with a removable protecting group.

9. The method of claim 7, wherein the second saccharide or oligosaccharide further comprises a protected thiol group of the formula —SR at the anomeric carbon of the reducing saccharide unit wherein R is a thiol group protecting agent.

10. The method of claim 9, wherein, after step iv), the thiol protecting group of the second saccharide or oligosaccharide is removed and steps iii) and iv) are repeated.

11. The method of claim 7, wherein the solid support is selected from the group consisting of silica, synthetic silicates, biogenic silicates, porous glass, hydrogels, silicate-containing minerals, synthetic polymers, polystyrene, polypropylene, polyethylene glycol, polyacrylamide and copolymers thereof including copolymers of polystyrene and polyethylene glycol and polyacrylamide and polyethylene glycol.

12. The method of claim 7, wherein the saccharide or saccharide units of the oligosaccharide are selected from the group consisting of D-galactose, L-galactose, D-glucose, D-mannose, D-xylose, D-gluconic acid, N-acetyl-D-glucosamine, N-acetyl-D-galactosamine, sialyic acid, iduronic acid, L-fucose, inositols, as well as deoxy, deoxyhalo, deoxyamino, acylated, phosphorylated and sulfated derivatives thereof.

* * * * *